(12) United States Patent  (10) Patent No.: US 9,268,914 B2
Hamada et al.  (45) Date of Patent: Feb. 23, 2016

(54) SAMPLE TESTING APPARATUS

(75) Inventors: Yuichi Hamada, Kobe (JP); Masaharu Shibata, Kobe (JP); Daigo Fukuma, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 718 days.

(21) Appl. No.: 12/823,833

(22) Filed: Jun. 25, 2010

(65) Prior Publication Data

US 2010/0332191 A1 Dec. 30, 2010

(30) Foreign Application Priority Data

Jun. 30, 2009 (JP) .................................. 2009-156257

(51) Int. Cl.
*G06F 17/40* (2006.01)
*G06F 19/00* (2011.01)

(52) U.S. Cl.
CPC .................................. *G06F 19/366* (2013.01)

(58) Field of Classification Search
CPC ................................................... G06F 19/366
USPC .................................. 702/187, 182, 183, 184
See application file for complete search history.

(56) References Cited

U.S. PATENT DOCUMENTS

| | | | |
|---|---|---|---|
| 2002/0169843 A1* | 11/2002 | Tsuneda | 709/206 |
| 2003/0078805 A1* | 4/2003 | Ng et al. | 705/2 |
| 2004/0093526 A1* | 5/2004 | Hirsch | 713/202 |
| 2007/0238181 A1* | 10/2007 | Lamont et al. | 436/50 |
| 2009/0172160 A1* | 7/2009 | Klein | 709/225 |

FOREIGN PATENT DOCUMENTS

| | | | |
|---|---|---|---|
| JP | 2006-030100 A | | 2/2006 |
| JP | 2006030100 A | * | 2/2006 |

* cited by examiner

*Primary Examiner* — Sujoy Kundu
*Assistant Examiner* — Ricky Ngon
(74) *Attorney, Agent, or Firm* — Brinks Gilson & Lione

(57) ABSTRACT

A sample testing apparatus comprising: a first storing section for storing identification information of an operator in association with first or second attribute information; an identification information receiving section for receiving an input of the identification information of the operator; a testing section for obtaining a test result by testing a sample; a second storing section for storing the test result of the sample so as to be linked with the received identification information; an operation end instruction receiving section for receiving an operation end instruction by the operator; and a deleting section for deleting from the second storing section the test result which is stored so as to be linked with the identification information received by the identification information receiving section in the case in which the received identification information is associated with the second attribute information when the operation end instruction is received.

15 Claims, 29 Drawing Sheets

FIG.25

| ID | PASSWORD | GROUP |
|---|---|---|
| user1 | 1234 | GENERAL USER |
| user2 | 5678 | GENERAL USER |
| service1 | 9012 | SERVICEMAN |
| abmin | 3456 | MANAGER |
| ⋮ | ⋮ | ⋮ |

FIG.26

| SAMPLE ID | WBC | RBC | ... | ID |
|---|---|---|---|---|
| 0001 | 4.8 | 4.0 | ... | user1 |
| 0002 | 5.1 | 3.9 | ... | user2 |
| 0003 | 3.8 | 5.0 | ... | user2 |
| 1001 | 6.3 | 4.5 | ... | service1 |
| ⋮ | ⋮ | ⋮ | ⋮ | ⋮ |

FIG.27

| DATE | TIME | CONTENT | ID |
|---|---|---|---|
| 2009/5/1 | 13:02 | SAMPLING ERROR | user1 |
| 2009/5/2 | 14:34 | PLEASE CHANGE PIERCER | user1 |
| 2009/5/2 | 15:28 | SAMPLING ERROR | user2 |
| 2009/5/3 | 17:35 | UNIT COVER HAS BEEN OPENED | service1 |
| ⋮ | ⋮ | ⋮ | ⋮ |

SAMPLE TESTING APPARATUS

RELATED APPLICATIONS

This application claims priority under 35 U.S.C. §119 to Japanese Patent Application No. 2009-156257 filed on Jun. 30, 2009, the entire content of which is hereby incorporated by reference.

BACKGROUND OF THE INVENTION

1. Field of the Invention

The present invention relates to a sample testing apparatus for testing a sample which is collected from a human subject.

2. Description of the Related Art

Japanese Laid-open Patent Publication No. 2006-030100 discloses a dispensing apparatus in which, regarding operator identification information, three authority levels for a general operator, a manager and a serviceman are set in advance and which receives entry of an ID from an operator and permits the operator to execute functions of the authority level corresponding to the entered ID. In addition, Japanese Laid-open Patent Publication No. 2006-030100 contains a description that this technique can be applied not only to the dispensing apparatus but also to an analysis apparatus.

When an ID corresponding to the general operator is entered, the dispensing apparatus permits an operator to execute functions for the general operator, when an ID corresponding to the manager is entered, the dispensing apparatus permits an operator to execute functions for the general operator and the manager, and when an ID corresponding to the serviceman is entered, the dispensing apparatus permits an operator to execute functions for the general operator, the manager and the serviceman. An operator having an ID corresponding to the serviceman performs an operation test of the apparatus as maintenance work and confirms whether the apparatus is operating normally on the basis of the operation history of the apparatus. A general operator and a manager are operators on the facility side having the above-described dispensing apparatus delivered thereto and a serviceman is an operator on the trader side delivering the above-described dispensing apparatus to the facility.

When the technique described in Japanese Laid-open Patent Publication No. 2006-030100 is applied to an analysis apparatus, a serviceman performs an analysis operation as maintenance work by using a control sample and confirms an analysis result to confirm whether the analysis apparatus is operating normally. Since the analysis result which is generated with the maintenance work is not necessary for operators on the facility side, the serviceman is required to delete the analysis result when the maintenance work ends.

However, in the analysis apparatus to which the technique described in Japanese Laid-open Patent Publication No. 2006-030100 is applied, the serviceman is permitted to execute functions of a general operator and a manager. Accordingly, there is a concern that analysis results which are obtained by an operator on the facility side may be deleted by mistake when the serviceman deletes the analysis result of the control sample which is generated with the maintenance work.

SUMMARY OF THE INVENTION

The scope of the present invention is defined solely by the appended claims, and is not affected to any degree by the statements within this summary.

A first aspect of the present invention is a sample testing apparatus comprising: a first storing section for storing identification information of an operator in association with first or second attribute information showing the attribute of the operator; an identification information receiving section for receiving an input of the identification information of the operator; a testing section for obtaining a test result by testing a sample; a second storing section for storing the test result of the sample, which is obtained by the testing section, so as to be linked with the identification information which is received by the identification information receiving section; an operation end instruction receiving section for receiving an operation end instruction by the operator; and a deleting section for deleting from the second storing section the test result which is stored so as to be linked with the identification information received by the identification information receiving section in the case in which the identification information received by the identification information receiving section is associated with the second attribute information when the operation end instruction is received by the operation end instruction receiving section.

A second aspect of the present invention is a sample testing apparatus comprising: a first storing section for storing identification information of an operator in association with first or second attribute information showing the attribute of the operator; an identification information receiving section for receiving an input of the identification information of the operator; a testing section for obtaining a test result by testing a sample; a second storing section for storing the test result of the sample, which is obtained by the testing section, so as to be linked with the identification information which is received by the identification information receiving section; and an editing prohibition section for prohibiting a process of editing the test result which is linked with the identification information associated with the first attribute information when the identification information received by the identification information receiving section is associated with the second attribute information.

A third aspect of the present invention is a sample testing apparatus, comprising a memory storing an identification information of an operator in association with first or second attribute information showing the attributer of the operator; a testing section for obtaining a test result by testing a sample; and a controller, wherein the controller is configured to: receive an input of an identification information of an operator; store the test result in the memory which is obtained by the testing section so as to be linked with the received identification information; receive an operation end instruction; and delete from the memory the test result which is stored so as to be linked with the received identification information associated with the second attribute information in the case in which the received identification information is associated with the second attribute information when receiving the operation end instruction.

A fourth aspect of the present invention is A sample testing apparatus, comprising a memory storing an identification information of an operator in association with first or second attribute information showing the attributer of the operator; a testing section for obtaining a test result by testing a sample; and a controller, wherein the controller is configured to: receive an input of an identification information of an operator; store the test result in the memory which is obtained by the testing section so as to be linked with the received identification information; and prohibit a process of editing the test result which is linked with the identification information associated with the first attribute information when the received identification information is associated with the second attribute information.

BRIEF DESCRIPTION OF THE DRAWINGS

FIG. 25 is a schematic diagram showing an operator information database according to the first embodiment;

FIG. 26 is a schematic diagram showing a test result database according to the first embodiment;

FIG. 27 is a schematic diagram showing an operation history database according to the first embodiment;

DETAILED DESCRIPTION OF THE PREFERRED EMBODIMENTS

First Embodiment

A sample testing apparatus according to a first embodiment of the invention is a blood cell analysis apparatus which classifies and counts the number of blood cell components such as red blood cells, white blood cells and platelets which are included in a blood sample gathered from a human subject.

Figure 1:
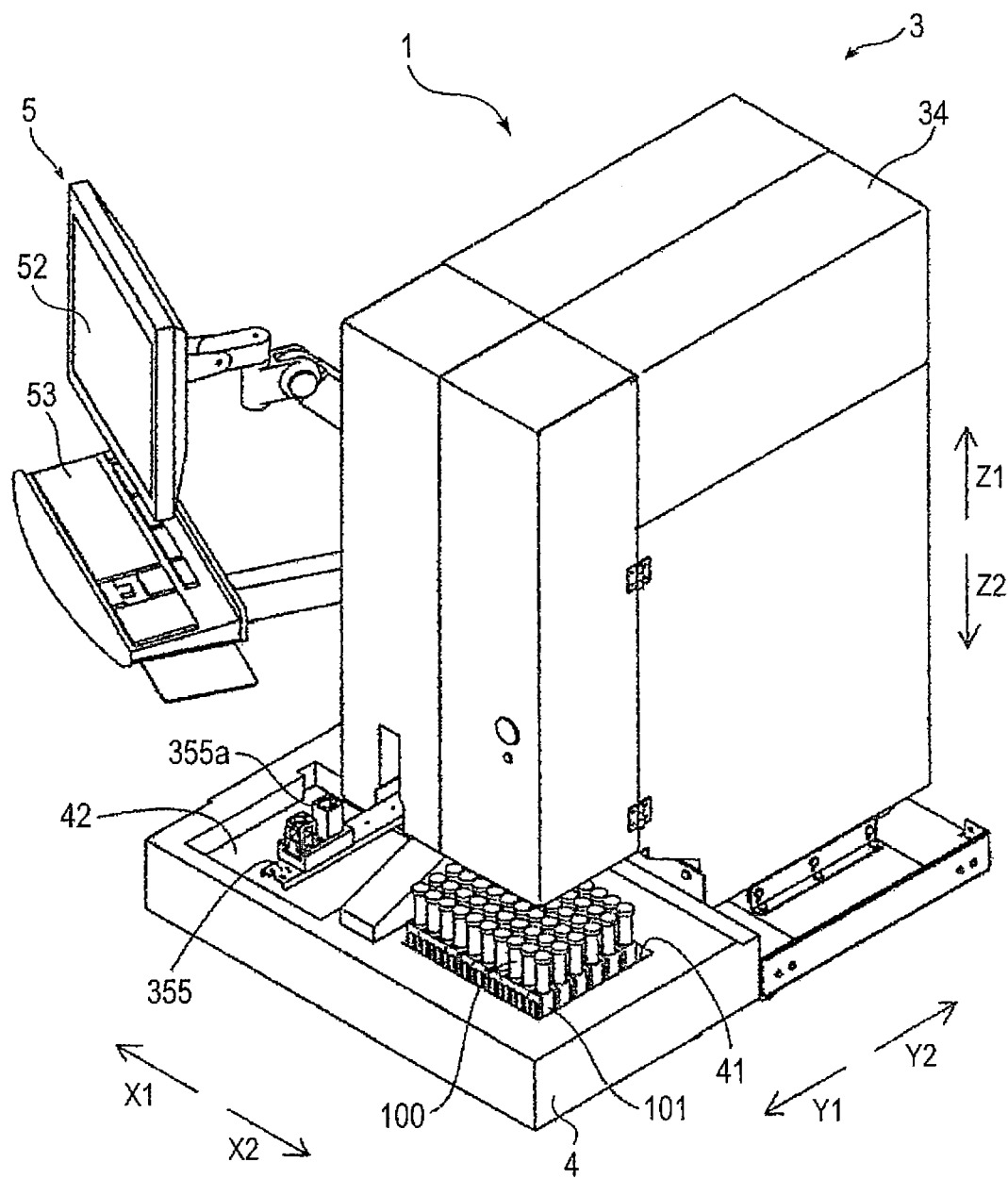
FIG. 1 is a perspective view showing the external configuration of a sample testing apparatus according to a first embodiment.

FIG. 1 is a perspective view showing the external configuration of a blood cell analysis apparatus 1. As shown in FIG. 1, the blood cell analysis apparatus 1 includes a measuring unit 3, a transport apparatus 4 which is disposed in front of the measuring unit 3 (in a direction of the arrow Y1) and a control apparatus 5 which is composed of a personal computer electrically connected to the measuring unit 3 and the transport apparatus 4. The control apparatus 5 includes a display section 52 and an input device 53. The display section 52 is provided to display analysis results and the like which are obtained by analyzing data of digital signals transmitted from the measuring unit 3.

The transport apparatus 4 includes a before-analysis rack holding section 41 which can hold a plurality of racks 101 accommodating sample containers 100 each containing a sample not yet analyzed, an after-analysis rack holding section 42 which can hold a plurality of racks 101 accommodating sample containers 100 each containing a sample subjected to an analysis, a rack transporting section which transversely transports a rack 101 in directions of the arrows X1 and X2, and a bar-code reading section which reads a bar-code 100b of a sample container 100 and a bar-code 101a adhered to a rack 101.

Figure 2:
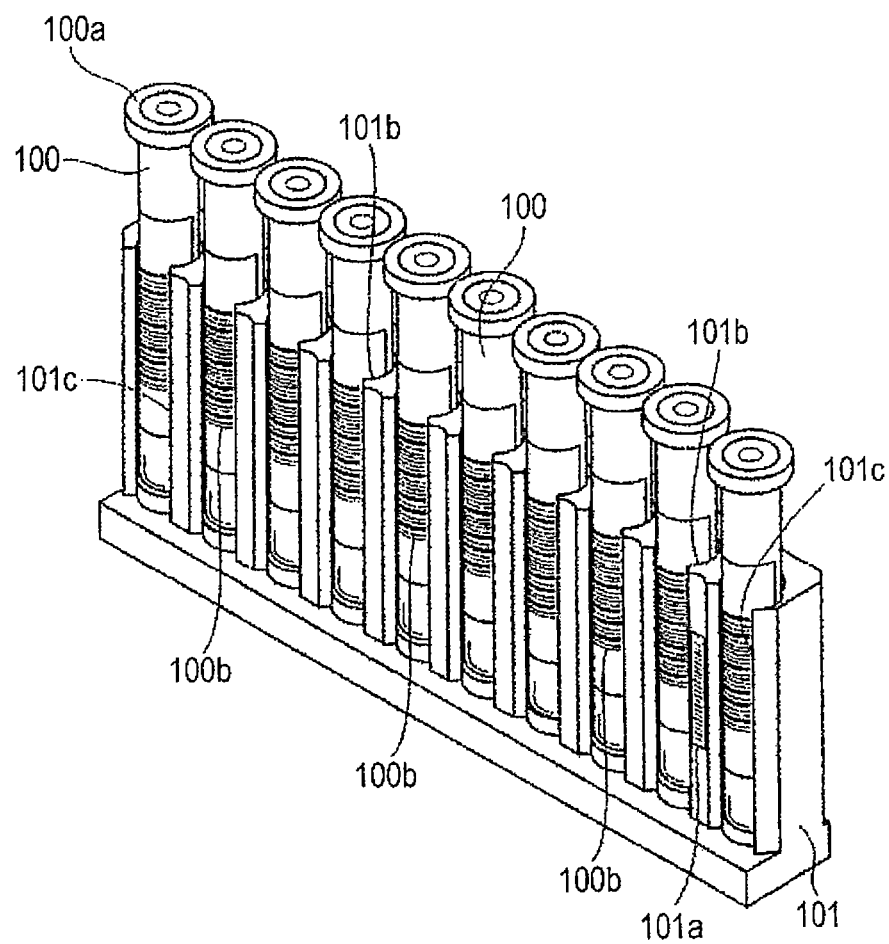
FIG. 2 is a perspective view showing the external configurations of a rack which holds sample containers and the sample containers which are held in the rack.

FIG. 2 is a perspective view showing the external configurations of a rack which holds sample containers and the sample containers which are held in the rack. As shown in FIG. 2, in a rack 101, ten container accommodating sections 101b are formed so that ten sample containers 100 are accommodated in a line. A bar-code 100b of each sample container 100 is uniquely adhered to each sample and is used for management of a test result of each sample. In addition, in each container accommodating section 101b, an opening section 101c is provided so as to visually check the bar-code 100b of the accommodated sample container 100. A bar-code 101a is uniquely adhered to each rack 101 and is used for management of test results of samples.

Figure 3:
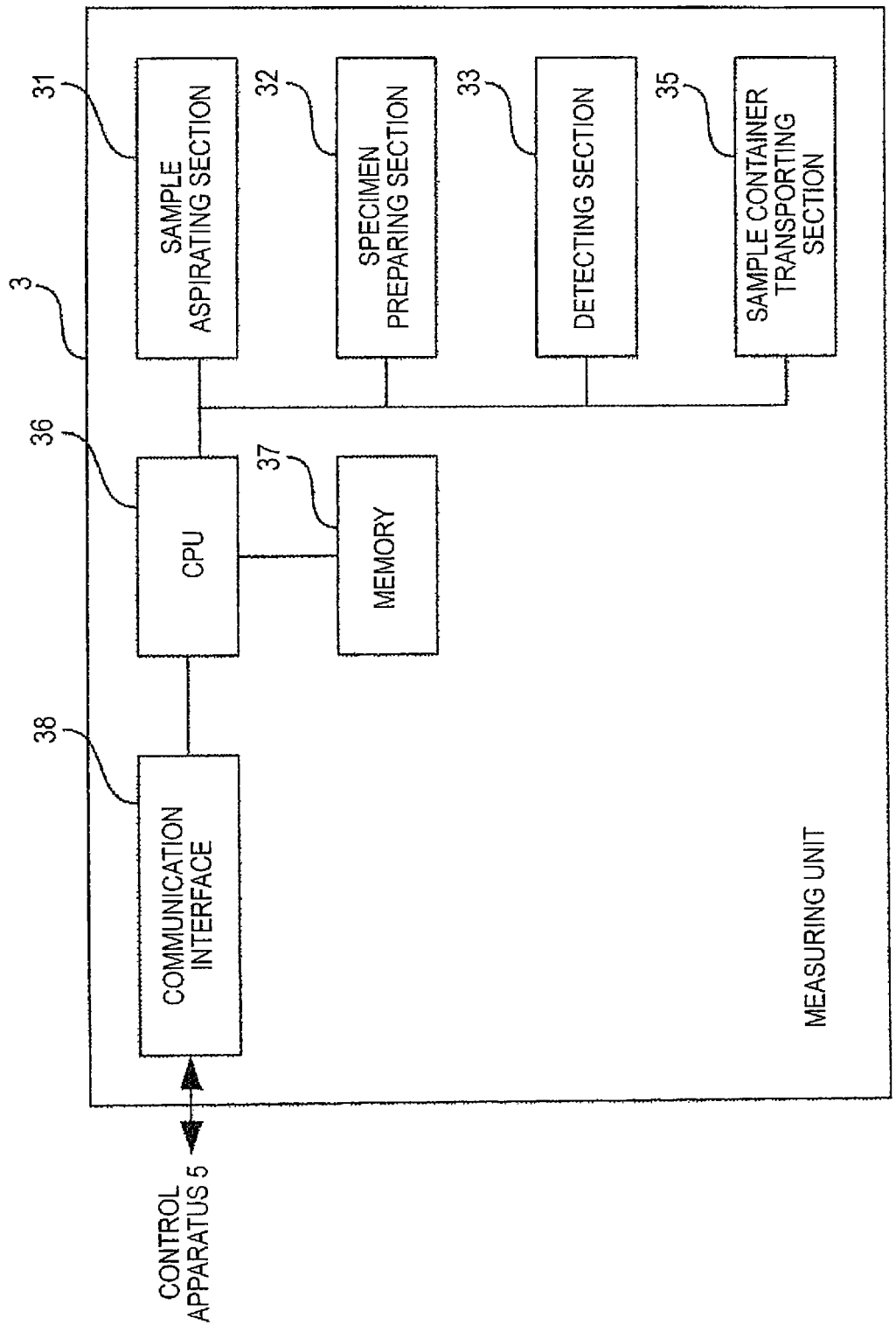
FIG. 3 is a block diagram showing the configuration of a measuring unit according to the first embodiment.

FIG. 3 is a block diagram showing the configuration of the measuring unit 3 of the blood cell analysis apparatus 1'. As shown in FIG. 3, the measuring unit 3 includes a sample aspirating section 31 for aspirating blood which is a sample from a sample container 100, a specimen preparing section 32 for preparing a detection specimen from the blood aspirated by the sample aspirating section 31 and a detecting section 33 for detecting blood cell components of the blood from the specimen prepared by the specimen preparing section 32. In addition, the measuring unit 3 further includes a unit cover 34 for accommodating the sample aspirating section 31, the specimen preparing section 32 and the like therein and a sample container transporting section 35 for introducing a sample container 100 into the unit cover 34 (see FIG. 1) to transport the sample container 100 to a position where the aspiration is carried out by the sample aspirating section 31. Moreover, the measuring unit 3 further includes a CPU 36 for controlling the sections, a memory 37 for storing programs which are executed by the CPU 36 and data which are used in the execution of the programs and a communication interface 38 which is connected to the control apparatus 5 so as to communicate therewith.

The detecting section 33 is configured to carry out RBC detection (detection of red blood cells) and PLT detection (detection of platelets) by a sheath-flow DC detection method and to carry out HGB detection (detection of hemochromes in blood) by a SLS-hemoglobin method. In addition, the detecting section 33 is configured to carry out WBC detection (detection of white blood cells) by a flow cytometry method using a semiconductor laser. The detection result obtained by the detecting section 33 is transmitted as measurement data to the control apparatus 5. This measurement data is the base of a final test result (the number of red blood cells, the number of platelets, quantity of hemoglobin, the number of white blood cells and the like) which is provided to a user.

The sample container transporting section 35 has a hand section (not shown) which can grasp a sample container 100, a bar-code reading section (not shown) and a sample container moving section 355 for horizontally moving a sample container 100 in directions of the arrows Y1 and Y2. The hand section is disposed above a transport path of a rack 101 which is transported by the transport apparatus 4. The sample container moving section 355 has a sample setting section 355a (see FIG. 1) and can allow the sample setting section 355a to dispose an aspiration position (not shown)

Figure 4:
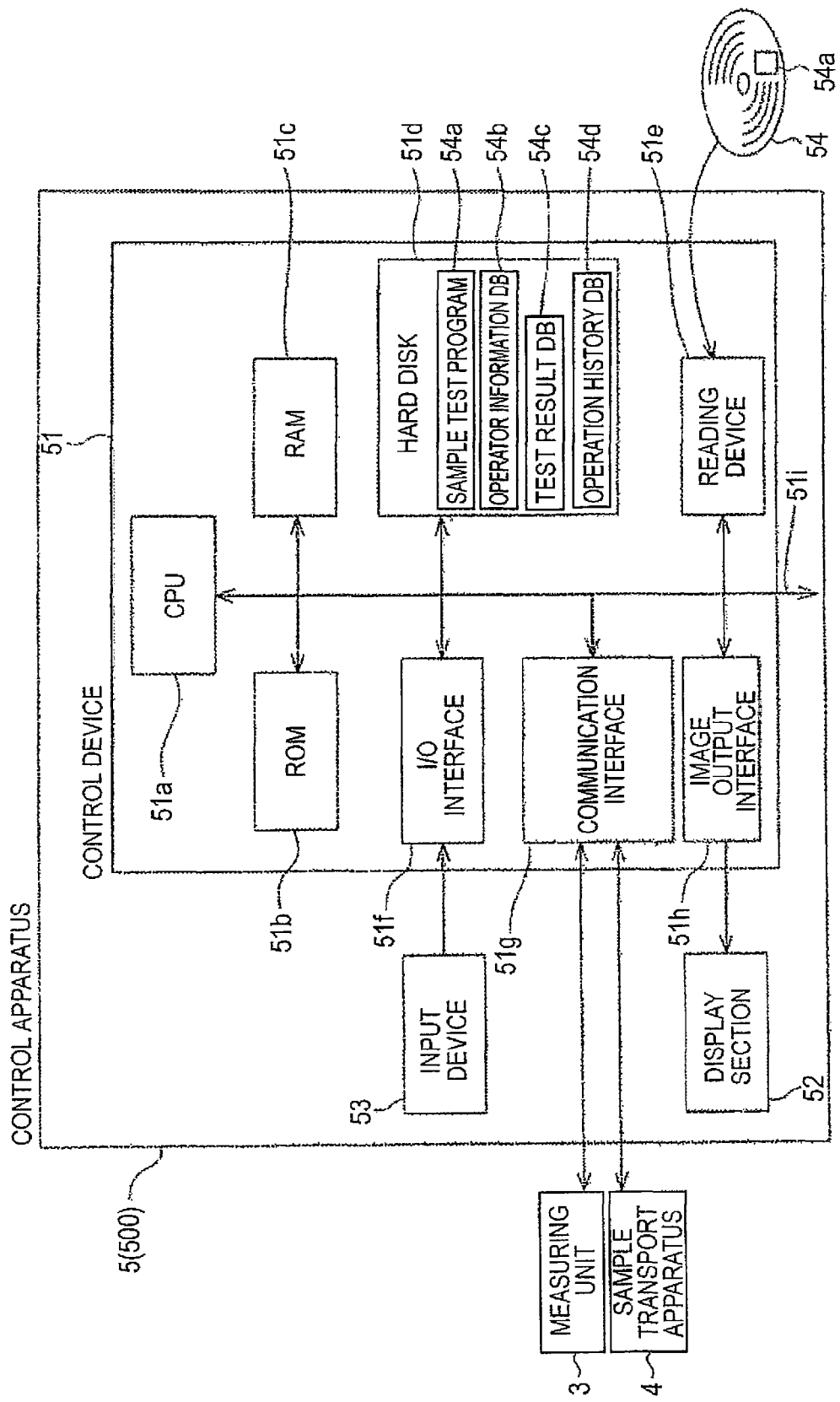
FIG. 4 is a block diagram showing the configuration of a control apparatus according to the first embodiment.

FIG. 4 is a block diagram showing the configuration of the control apparatus 5 of the blood cell analysis apparatus 1. As shown in FIG. 4, the control apparatus 5 is composed of a computer 500 mainly including a control device 51, the display section 52 and the input device 53.

As shown in FIG. 4, the control device 51 mainly includes a CPU 51a, a ROM 51b, a RAM 51c, a hard disk 51d, a reading device 51e, an I/O interface 51f, a communication interface 51g and an image output interface 51h. The CPU 51a, ROM 51b, RAM 51c, hard disk 51d, reading device 51e, I/O interface 51f, communication interface 51g and image output interface 51h are connected to each other by a bus 51i.

The CPU 51a can execute computer programs which are stored in the ROM 51b and computer programs which are loaded to the RAM 51c. The computer 500 functions as the control apparatus 5 by executing an application program 54a to be described later with the CPU 51a.

The ROM 51b is composed of a mask ROM, a PROM, an EPROM, an EEPROM or the like, and computer programs which are executed by the CPU 51a and data which are used in the execution of the programs are recorded therein.

The RAM 51c is composed of a SRAM, a DRAM or the like. The RAM 51c is used to read computer programs which are recorded in the ROM 51b and the hard disk 51d. In addition, the RAM is used as a work area of the CPU 51a when these computer programs are executed.

In the hard disk 51d, various computer programs for execution by the CPU 51a, such as an operating system and an application program, and data which are used to execute the computer programs, are installed. The sample test program 54a for the control apparatus 5 is also installed in the hard disk 51d. In addition, the hard disk 51d is provided with an operator information database 54b, a test result database 54c and an operation history database 54d. Detailed descriptions of the databases will be described later.

The reading device 51e is composed of a flexible disk drive, a CD-ROM drive, a DVD-ROM drive or the like and can read computer programs or data which are recorded in a portable recording medium 54. In addition, the application program 54a is stored in the portable recording medium 54 and the computer 500 can read the application program 54a from the portable recording medium 54 and install the application program 54a in the hard disk 51d.

The above-described application program 54a is provided by the portable recording medium 54 and can be also provided from an external device, which is connected to the computer 500 by an electric communication line (which may be wired or wireless) to communicate therewith, through the electric communication line. For example, the application program 54a is stored in a hard disk of a server computer on the internet and the computer 500 accesses the server computer to download the application program 54a and install the application program in the hard disk 51d.

Further, in the hard disk 51d, for example, an operating system for providing a graphic user interface environment, such as Windows (registered trade name) which is made and distributed by Microsoft Corporation in America, is installed. In the following description, the application program 54a operates on the above-described operating system.

The I/O interface 51f is composed of, for example, a serial interface such as USB, IEEE1394 or RS-232C, a parallel interface such as SCSI, IDE or IEEE1284, and an analog interface including a D/A converter and an A/D converter. The input device 53 is connected to the I/O interface 51f and a user uses the input device 53 so as to input data to the computer 500.

For example, the communication interface 51g is an Ethernet (registered trade name) interface. The computer 500 uses a predetermined communication protocol by the communication interface 51g so as to transmit and receive data to and from the measuring unit 3 and the transport apparatus 4.

The image output interface 51h is connected to the display section 52 composed of an LCD or a CRT so as to output to the display section 52 a picture signal corresponding to image data provided from the CPU 51a. The display section 52 is configured to display an image (screen) in accordance with an input picture signal.

Figure 5:
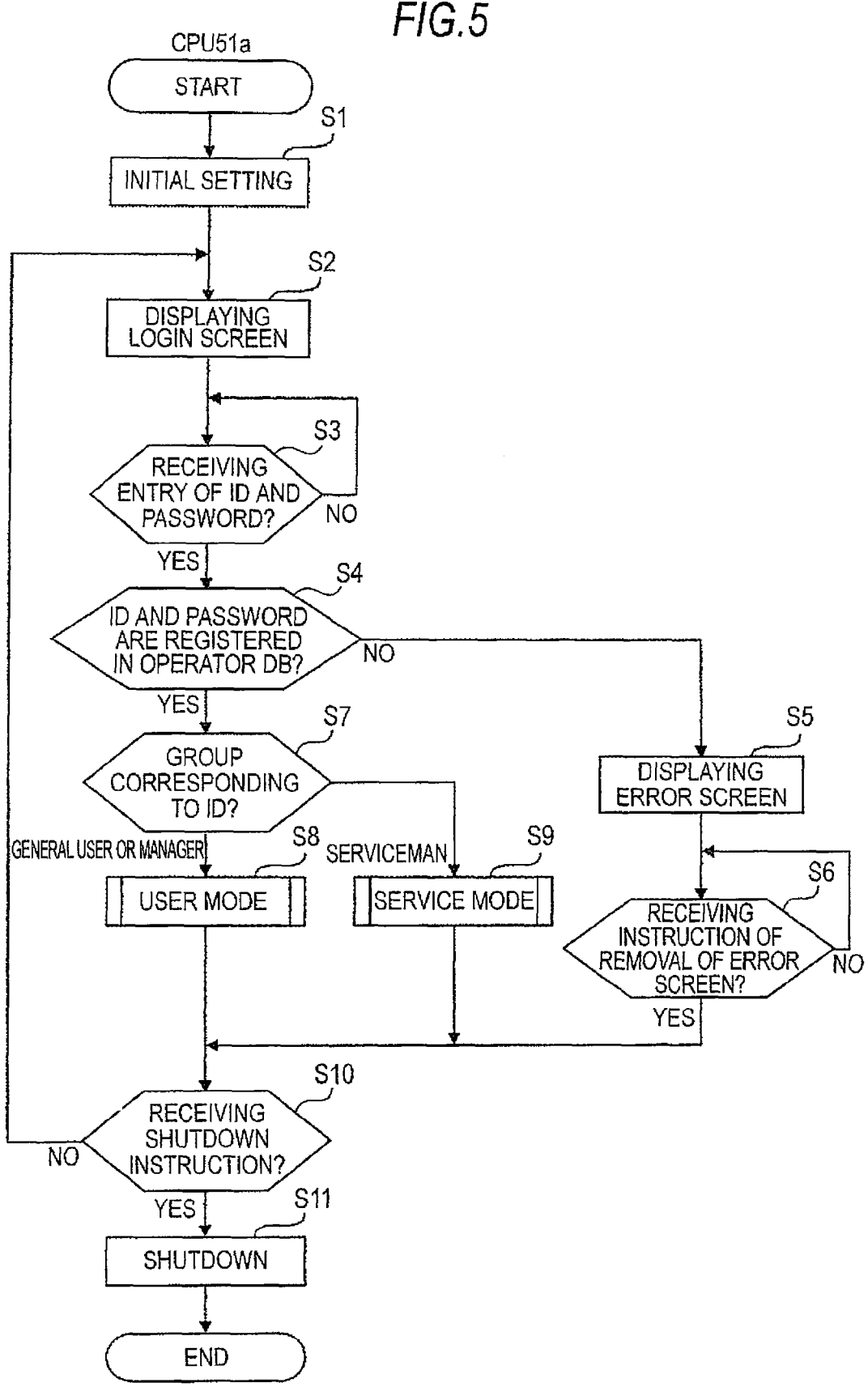
FIG. 5 is a flowchart showing a sample testing process of the control apparatus according to the first embodiment.

FIG. 5 is a flowchart showing a sample testing process of the control apparatus 5 of the blood cell analysis apparatus 1. Hereinafter, the sample testing process of the control apparatus 5 (CPU 51a) according to this embodiment will be described with reference to FIG. 5.

First, in Step S1, the CPU 51a executes an initial setting process. Next, in Step S2, the CPU 51a displays a login screen F (see FIG. 6) on the display section 52.

Figure 6:
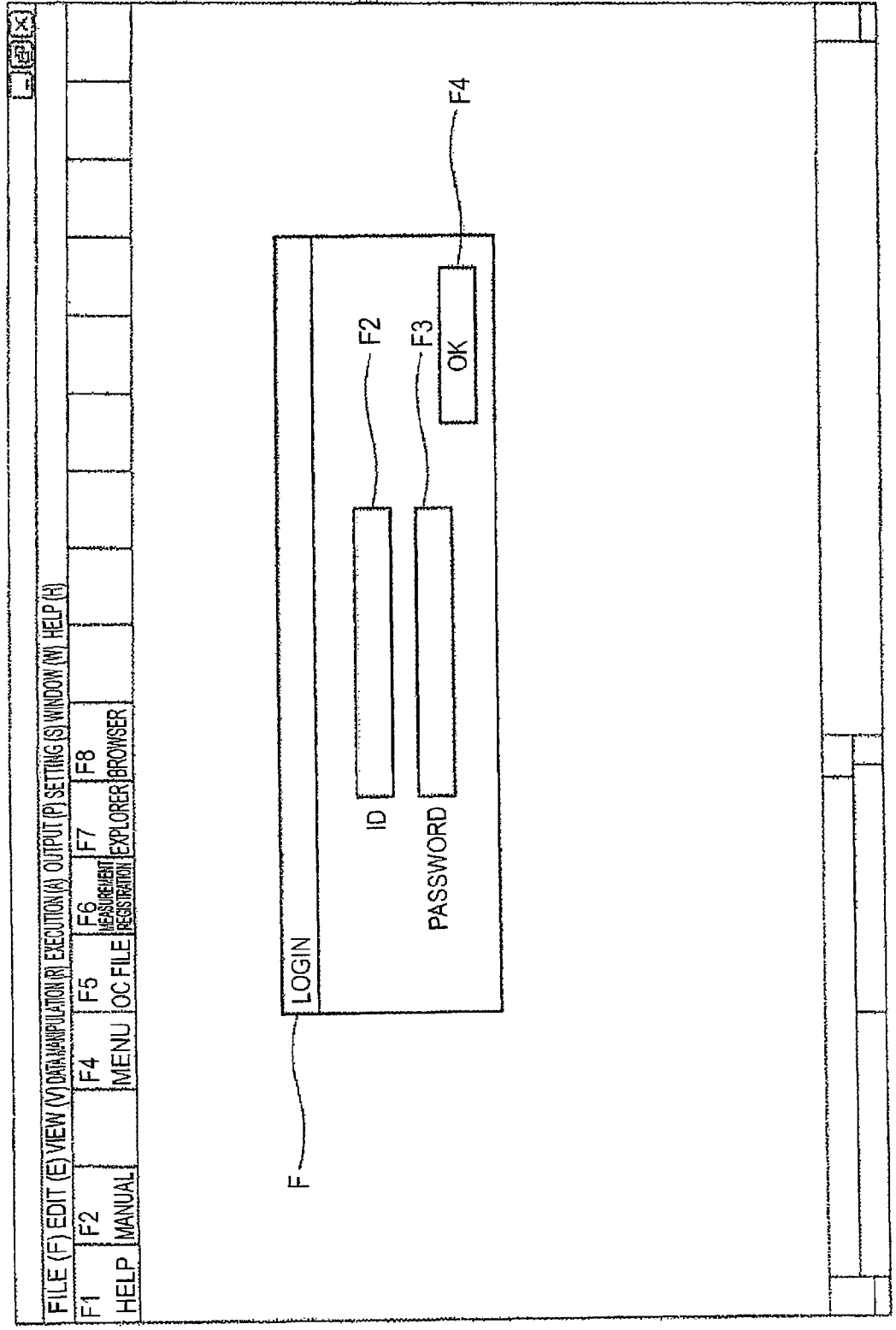
FIG. 6 is a diagram showing an example of a login screen which is displayed on a display section according to the first embodiment.

FIG. 6 is a diagram showing an example of the login screen F which is displayed on the display section 52. As shown in FIG. 6, the login screen F includes an ID field F2, a password field F3 and an OK button F4. An operator enters an ID and a password in the ID field F2 and the password field F3 by the input device 53 and selects the OK button F4 to confirm the entry of ID and password. Herein, the ID is identification information for identifying the operator.

Returning to FIG. 5, in Step S3, the CPU 51*a* determines whether the entry of ID and password has been received. When it is determined that the entry of ID and password has been received (YES in Step S3), the CPU 51*a* determines in Step S4 whether the received ID and the password corresponding to the ID are registered in the operator information database 54*b*.

FIG. 25 is a schematic diagram showing the operator information database 54*b* which is provided in the hard disk 51*d*. The operator information database 54*b* is a relational database and includes fields of ID, password and group as shown in FIG. 25. The ID is information that is uniquely set for each operator and is used to specify an operator. The password is set by an operator. The group is information showing which of the three groups of general user, serviceman and manager an operator belongs to. In the blood cell analysis apparatus 1 according to this embodiment, executable functions vary depending on the group of an operator.

An operator belonging to the general user group (hereinafter, referred to as a general user) is an operator of the facility having the blood cell analysis apparatus 1 installed therein and carries out a test of a sample gathered from a human subject. The ID and password of the general user are registered in the operator information database 54*b* in a general user registration screen (not shown) by an operator belonging to the manager group (hereinafter, referred to as a manager). The general user can execute various processes, such as measurement of samples in the blood cell analysis apparatus 1, registration of measurements, changing and deletion of test results, validation (approval) of test results, external output of a display screen and changing of settings, in the range set by the manager.

The manager is an operator on the facility side having the blood cell analysis apparatus 1 installed therein and mainly performs the management of general users of the blood cell analysis apparatus 1. The ID and password of the manager are registered in the operator information database 54*b* by an operator belonging to the serviceman group (hereinafter, referred to as a serviceman). As described above, the manager can set which functions can be executed among the various functions of the blood cell analysis apparatus 1 for each general user. In addition, the manager can execute all the functions, which can be executed by a general user, of the blood cell analysis apparatus 1.

The serviceman is an operator on the trader side delivering the blood cell analysis apparatus 1 to the facility and mainly performs maintenance work of the blood cell analysis apparatus 1. The serviceman can execute functions such as changing of settings which cannot be changed by a general user or a manager. As functions relating to the maintenance of the blood cell analysis apparatus 1, the serviceman can execute the setting of an error monitoring range by the apparatus, the setting of an error skip function and the like. In addition, the serviceman can execute all the functions, which can be executed by a general user, of the blood cell analysis apparatus 1. However, the serviceman cannot change and delete test results and operation histories obtained by a general user. This will be described later.

Returning to FIG. 5, when it is determined that the received ID and the password corresponding to the ID are not registered in the operator information database 54*b* (NO in Step S4), the CPU 51*a* displays an error screen (see FIG. 7) J informing the operator of the determination on the display section 52 (Step S5).

Figure 7:
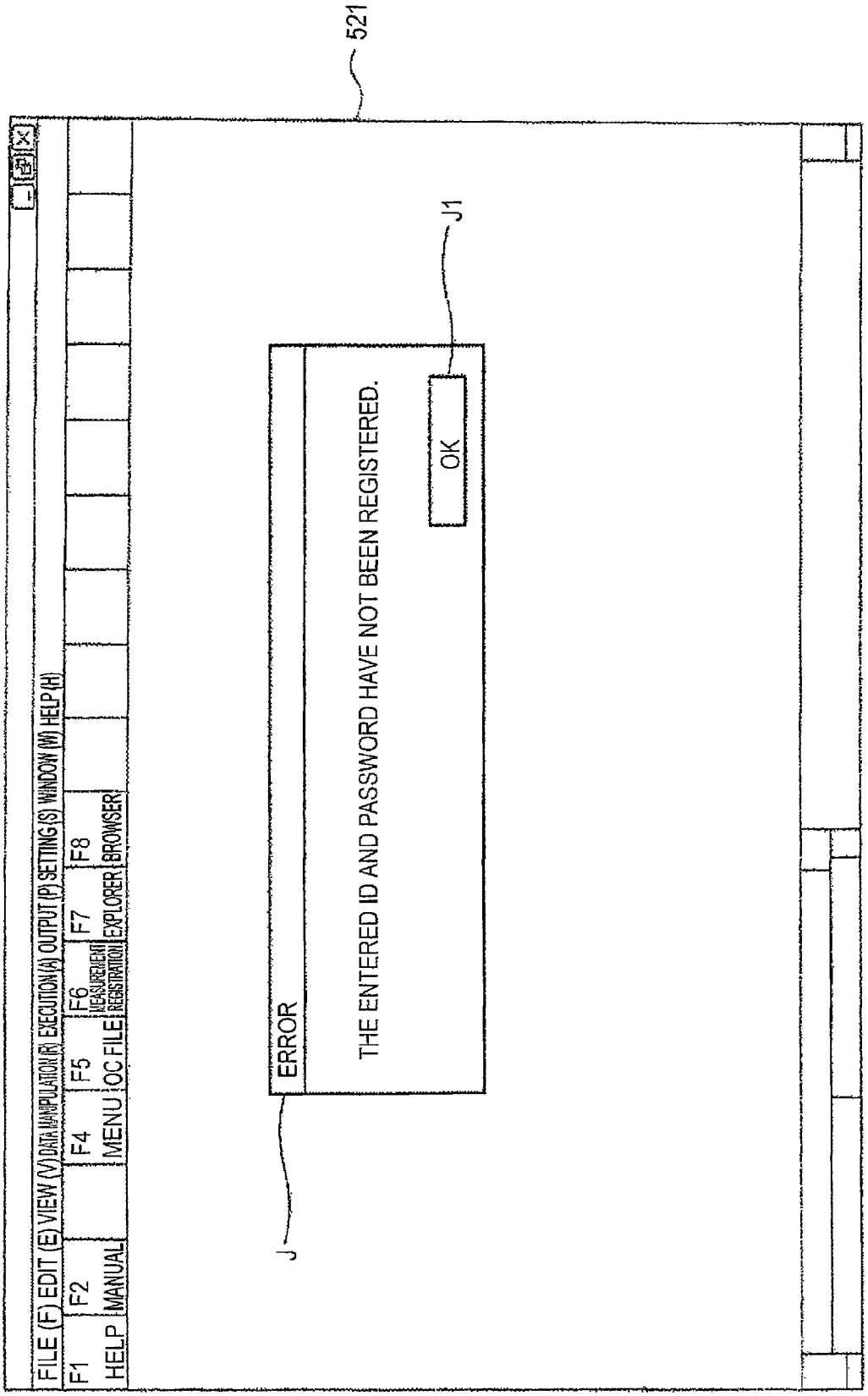
FIG. 7 is a diagram showing an example of an error screen which is displayed on the display section according to the first embodiment.

FIG. 7 is a diagram showing an example of the error screen J which is displayed on the display section 52. As shown in FIG. 7, the message "the entered ID and password have not been registered" is displayed in the error screen J. Further, the error screen J includes an OK button J1. The operator selects the OK button J1 by the input device 53 so as to instruct the removal of the error screen.

Returning to FIG. 5, in Step S6, the CPU 51*a* determines whether the instruction of the removal of the error screen has been received. When it is determined that the instruction of the removal of the error screen has been received (YES in Step S13), the CPU 51*a* removes the error screen J displayed on the display section 52 by executing an error screen removing process. Then, the CPU 51*a* executes a process of Step S10 to be described later.

When it is determined that the received ID and the password corresponding to the ID are registered in the operator information database 54*b* (YES in Step S4), the CPU 51*a* determines a group corresponding to the received ID by referring to the operator information database 54*b* in Step S7. When the group corresponding to the received ID is a general user group or a manager group (general user or manager in Step S7), the CPU 51*a* performs a process of Step S8. In Step S8, the blood cell analysis apparatus 1 operates in the range of functions corresponding to the general user group or the manager group. Hereinafter, the process of the CPU 51*a* in Step S8 will be called a user mode. When the group corresponding to the received ID is a serviceman group (serviceman in Step S7), the CPU 51*a* performs a process of Step S9. In Step S9, the blood cell analysis apparatus 1 operates in the range of functions corresponding to the serviceman group. Hereinafter, the process of the CPU 51*a* in Step S9 will be called a service mode. Processes of the CPU 51*a* in a user mode and in a service mode will be described later in detail.

Next, in Step S10, the CPU 51*a* determines whether an instruction of shutdown from the operator has been received. When it is determined that the instruction of shutdown has been received (YES in Step S10), the CPU 51*a* executes a shutdown process in Step S11. When it is determined that the instruction of shutdown has not been received (NO in Step S10), the CPU 51*a* executes the process of Step S2.

Figure 8:
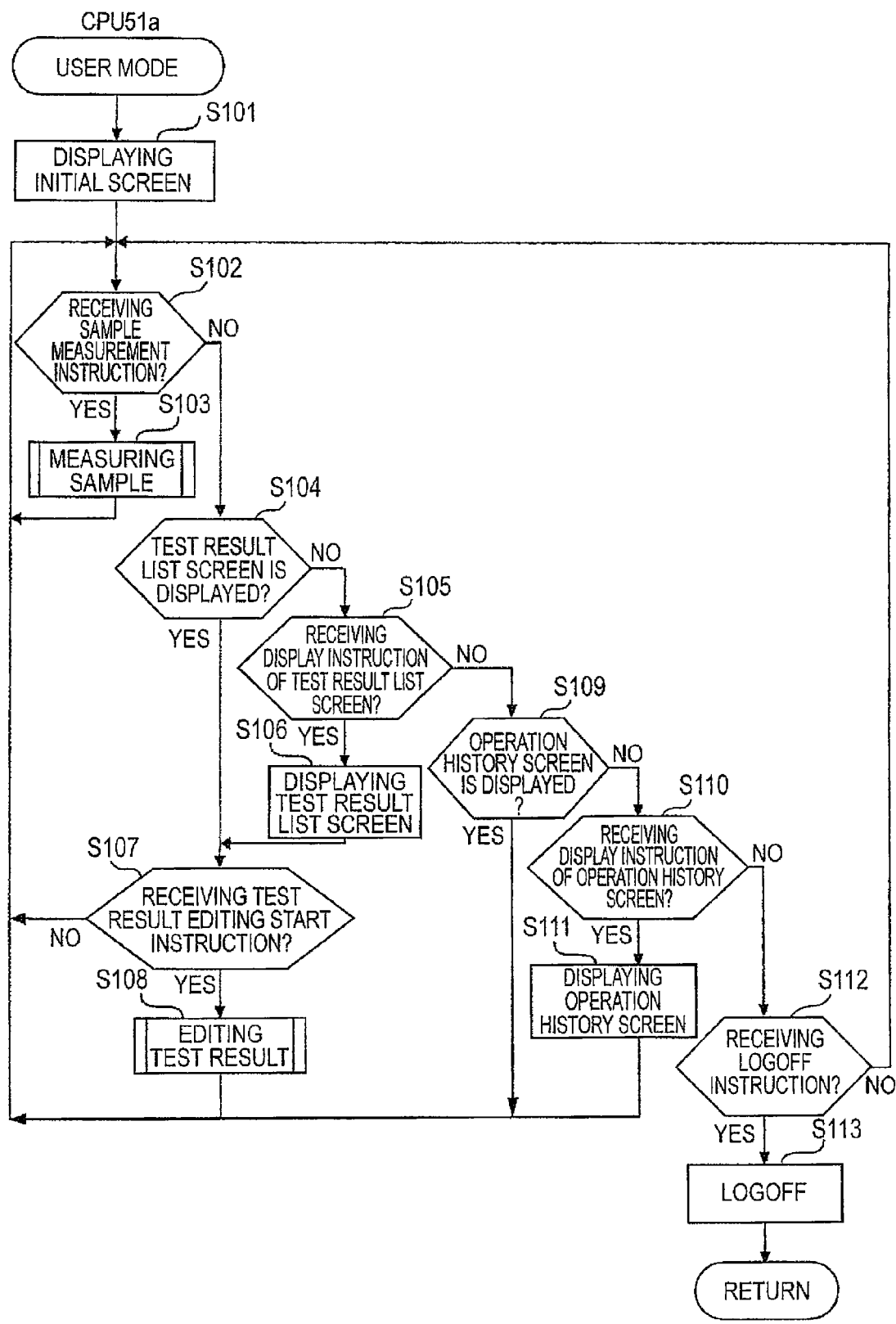
FIG. 8 is a flowchart showing a process of a CPU in a user mode according to the first embodiment.

FIG. 8 is a flowchart showing a process of the CPU 51*a* in a user mode. Hereinafter, the process of the control apparatus 5 (CPU 51*a*) in a user mode will be described with reference to FIG. 8. In the following description, a general user is set by a manager so as to execute at least the functions of changing and deletion of test results.

In Step S101, the CPU 51*a* displays an initial screen 521 (see FIG. 9) on the display section 52.

Figure 9:
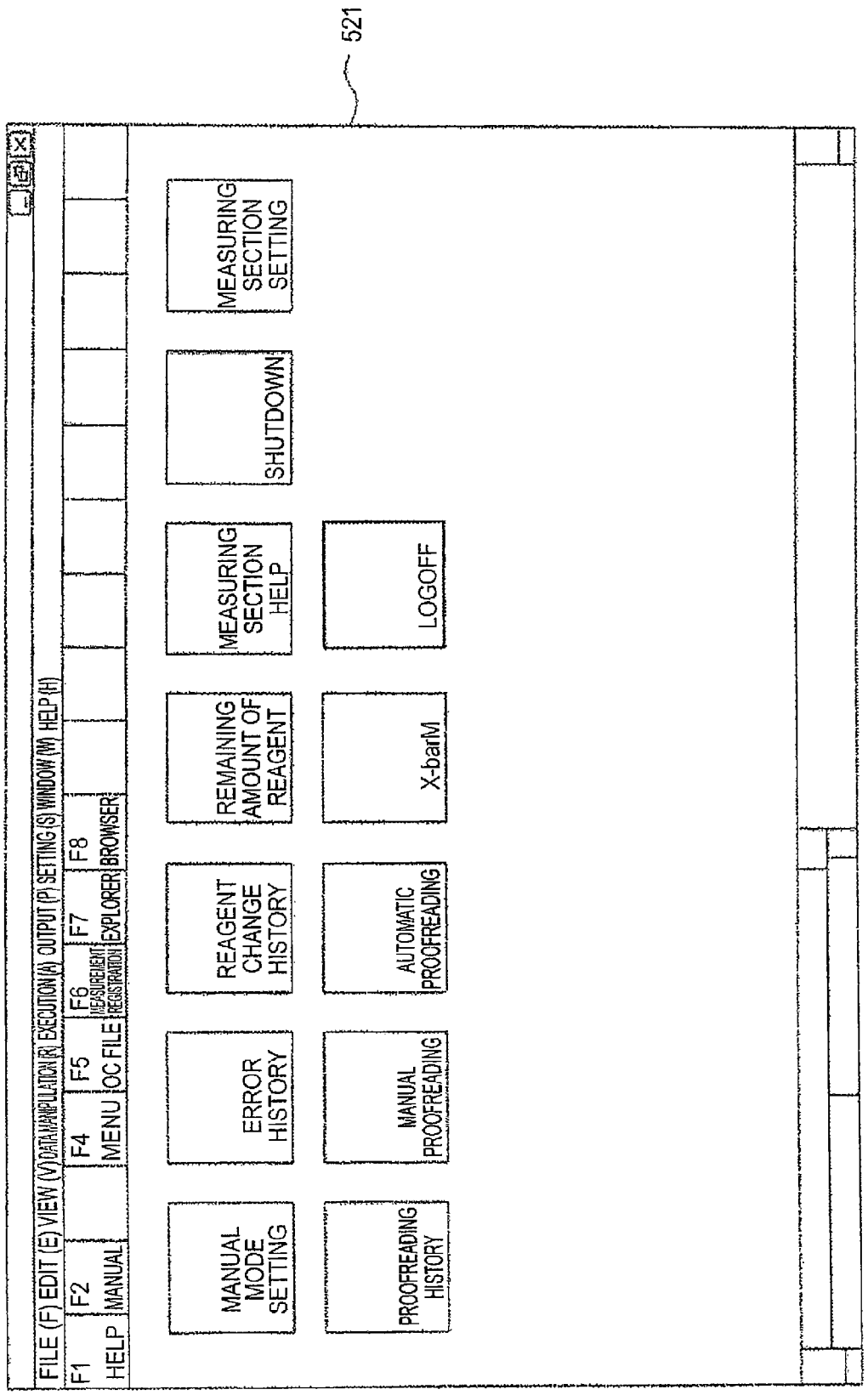
FIG. 9 is a diagram showing an example of an initial screen which is displayed on the display section in a user mode according to the first embodiment.

FIG. 9 is a diagram showing an example of the initial screen 521 which is displayed on the display section 52 in a user mode. As shown in FIG. 9, the initial screen 521 includes various buttons for instructing the CPU 51*a* so as to execute processes, such as measurement of samples, display of a setting screen, display of test results, display of operation histories and instructions of logoff and shutdown. An operator selects the above-described various buttons by the input device 53 so as to instruct the CPU 51*a* of the various processes.

Next, in Step S102, the CPU 51*a* determines whether an instruction of sample measurement from the operator has been received. When it is determined that the instruction of sample measurement has been received (YES in Step S102), the CPU 51*a* executes a sample measurement process in Step S103.

Figure 10:
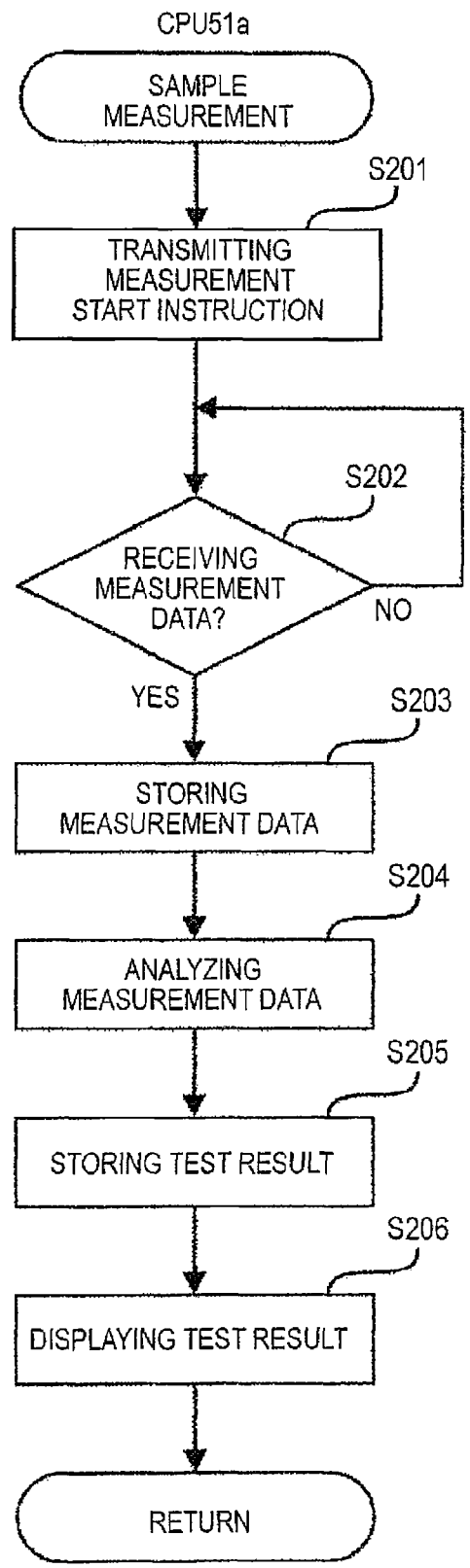
FIG. 10 is a flowchart showing a sample measurement process according to the first embodiment.

FIG. 10 is a flowchart showing a sample measurement process of the control apparatus 5 of the blood cell analysis apparatus 1. Hereinafter, the sample measurement process of the control apparatus 5 (CPU 51a) will be described with reference to FIG. 10.

First, in Step S201, the CPU 51a transmits an instruction for starting the measurement of a sample to the measuring unit 3. Sample measurement operations of the measuring unit 3 will be described later in detail. Next, in Step S202, the CPU 51a determines whether measurement data transmitted from the measuring unit 3 has been received. When it is determined that the measurement data has been received (YES in Step S202), the CPU 51a executes a process of storing the received measurement data in the RAM 51c in Step S203. Next, in Step S204, the CPU 51a obtains a test result by analyzing the measurement data stored in the RAM 51c. Next, in Step S205, the CPU 51a stores the obtained test result together with the ID of the operator in the test result database 54c provided in the hard disk 51d.

FIG. 26 is a schematic diagram showing the test result database 54c which is provided in the hard disk 51d. The test result database 54c is a relational database and includes fields of sample ID, WBC, RBC, . . . and ID as shown in FIG. 26. The sample ID is identification information that is uniquely set for each sample contained in a sample container 100. The WBC and the RBC are test items and indicate the number of white blood cells and the number of red blood cells in blood, respectively. The test items are not limited to the WBC and the RBC and may include the number of platelets and quantity of hemoglobin in blood. The ID indicates the ID of the operator of the apparatus when the test result is obtained.

Returning to FIG. 10, in Step S206, the CPU 51a executes a process of displaying on the display section 52 a test result display screen B (see FIG. 11) showing the test results stored in the test result database 54c.

Figure 11:
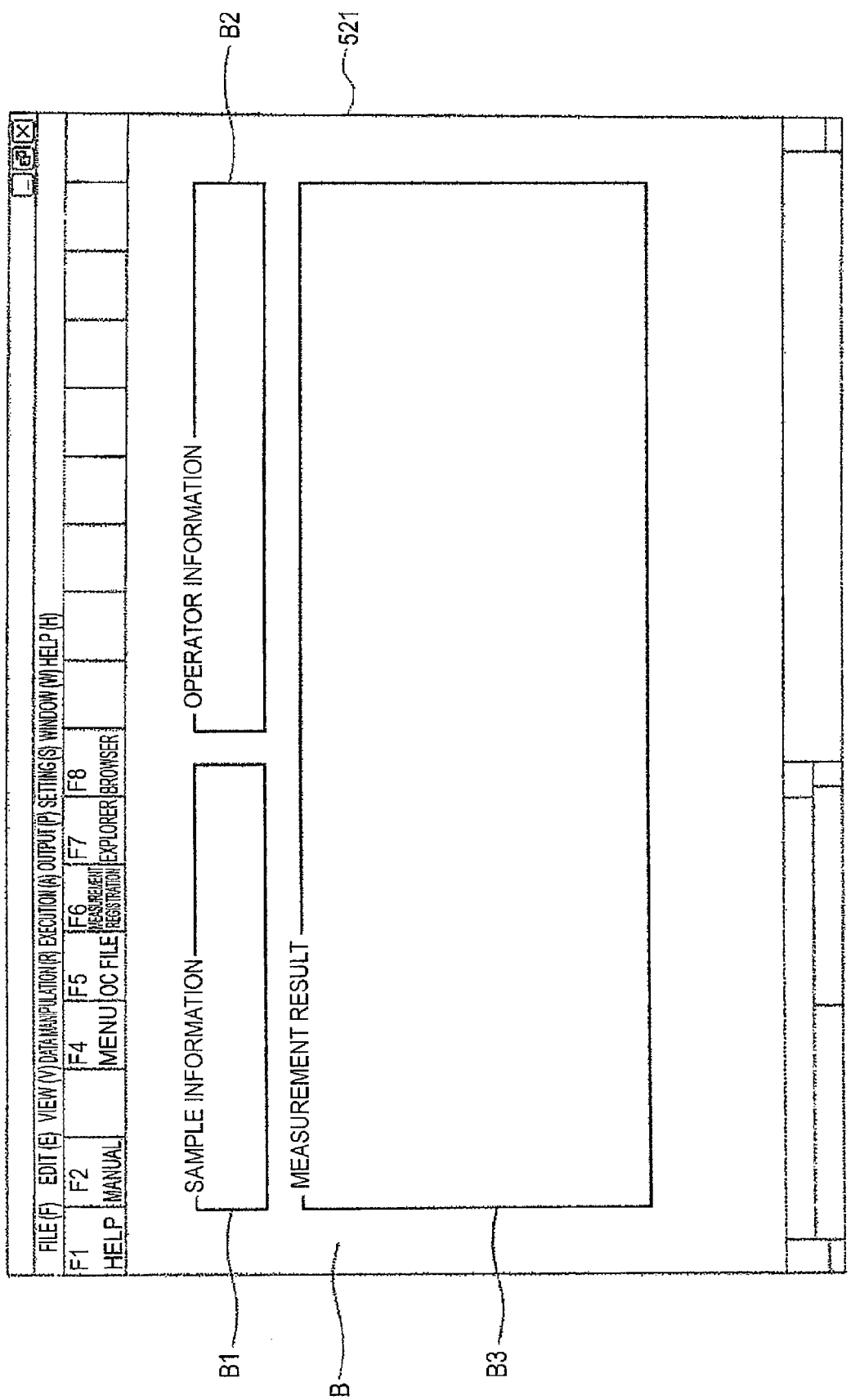
FIG. 11 is a diagram showing an example of a measurement result screen which is displayed on the display section in a user mode according to the first embodiment.

FIG. 11 is a diagram showing an example of the test result display screen B which is displayed on the display section 52 in a user mode. As shown in FIG. 11, the test result display screen B includes a sample information field B1 in which an ID of the sample and the like are displayed, an operator information field B2 in which an ID of the operator executing the test and the like are displayed and a measurement result field B3 in which test items of the sample are displayed. When a predetermined time elapses after the display of the test result display screen B on the display section 52, the CPU 51a executes the process of Step S102 of the flowchart shown in FIG. 8.

Figure 12:
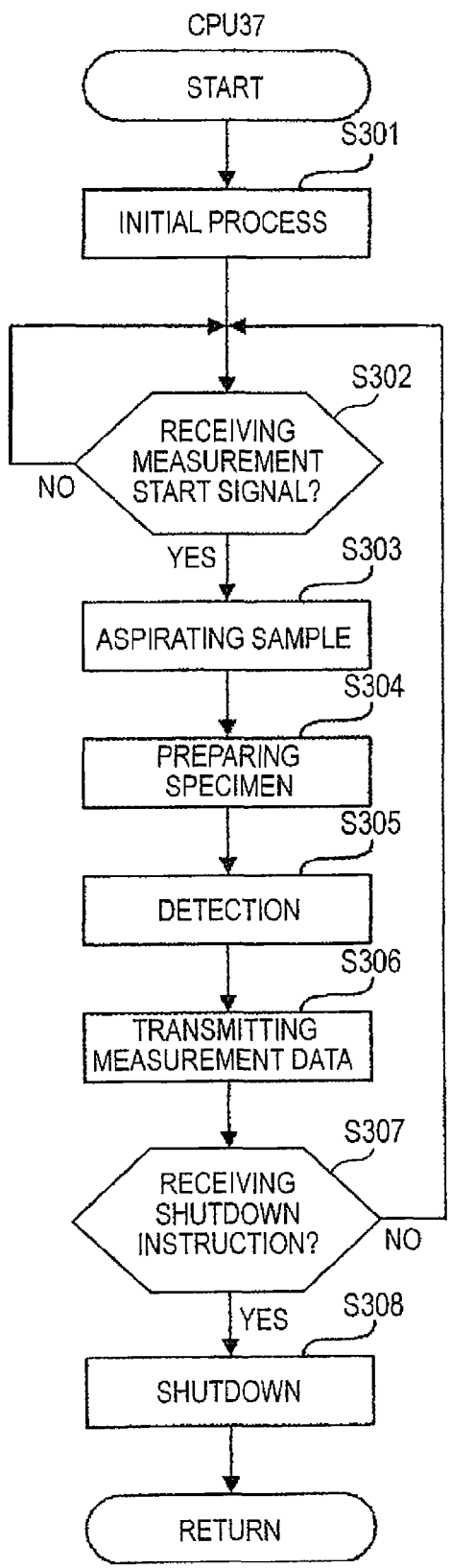
FIG. 12 is a flowchart showing sample measurement operations of the measuring unit according to the first embodiment.

FIG. 12 is a flowchart showing sample measurement operations of the measuring unit 3 of the blood cell analysis apparatus 1. Hereinafter, the sample measurement operations of the measuring unit 3 will be described with reference to FIG. 12.

First, in Step S301, the CPU 36 executes an initial process and returns the sections in the measuring unit 3 to respective initial operation positions. Next, in Step S302, the CPU 36 determines whether a measurement start instruction transmitted from the control apparatus 5 has been received. When it is determined that the measurement start instruction has been received (YES in Step S302), the CPU 36 controls the sample aspirating section 31 so as to aspirate a sample from a sample container 100 transported to the aspiration position in Step S303. Next, in Step S304, the CPU 36 controls the specimen preparing section 32 so as to prepare a detection specimen from the aspirated sample. Next, in Step S305, the CPU 36 controls the detecting section 33 so as to detect components of an analysis target from the detection specimen. Next, in Step S306, the CPU 36 transmits measurement data to the control apparatus 5.

Next, in Step S307, the CPU 36 determines whether a shutdown instruction from the control apparatus 5 has been received. When it is determined that the shutdown instruction is not received (NO in Step S307), the CPU 36 executes the process of Step S302. When it is determined that the shutdown instruction has been received (YES in Step S307), the CPU 36 transmits an operation history to the control apparatus 5 and executes a shutdown process in Step S308.

The CPU 51a receives the operation history transmitted from the measuring unit 3 and stores the received operation history together with the ID of the operator in the operation history database 54d provided in the hard disk 51d.

FIG. 27 is a schematic diagram showing the operation history database 54d which is provided in the hard disk 51d. The operation history database 54d is a relational database and includes fields of date, time, contents and ID as shown in FIG. 27. The date indicates a date at which the operation history is generated. The time indicates time at which the operation history is generated. The contents indicate the contents of the operation history (error or the like). The ID indicates an ID of the operator operating apparatus when the operation history is generated.

Returning to FIG. 8, when it is determined that the instruction of sample measurement is not received (NO in Step S102), the CPU 51a determines in Step S104 whether a test result list screen E (see FIG. 13) is displayed on the display section 52. When the test result list screen E is not displayed on the display section 52 (NO in Step S104), the CPU 51a determines in Step S105 whether an instruction for displaying the test result list screen E has been received. When it is determined that the instruction for displaying the test result list screen E has been received (YES in Step S105), the CPU 51a displays the test result list screen E on the display section 52 in Step S106.

Figure 13:
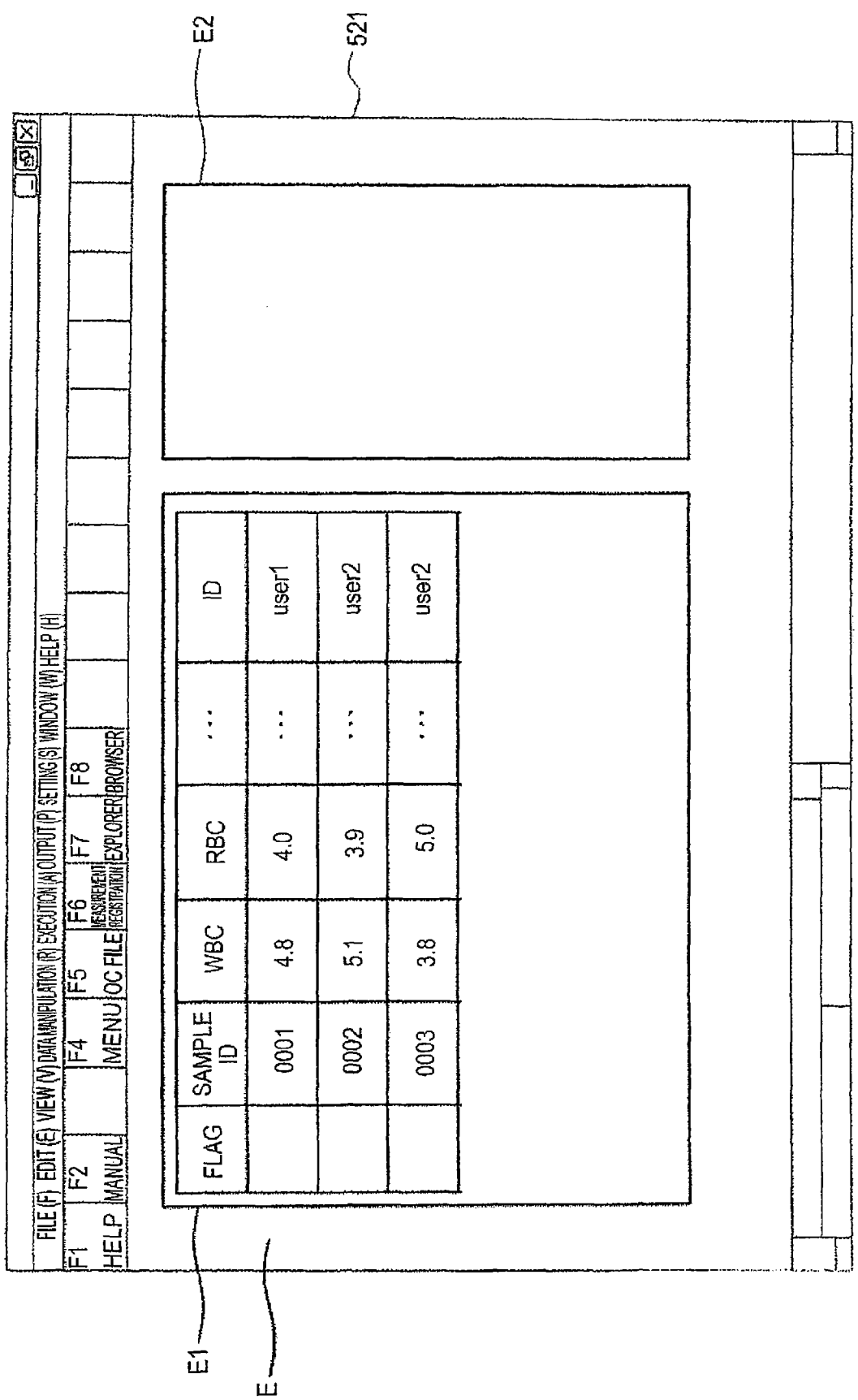
FIG. 13 is a diagram showing an example of a test result list screen which is displayed on the display section in a user mode according to the first embodiment.

FIG. 13 is a diagram showing an example of the test result list screen E which is displayed on the display section 52 in a user mode. As shown in FIG. 13, the test result list screen E includes an outline display field E1 in which outlines of test results are displayed and a detailed display field E2 in which the test result selected in the outline display field E1 is displayed in detail.

Returning to FIG. 8, when the test result list screen E is displayed on the display section 52 (YES in Step S104) and when the test result list screen E is caused to be displayed on the display section 52, the CPU 51a determines in Step S107 whether a measurement result editing start instruction has been received. When it is determined that the measurement result editing start instruction is not received (NO in Step S107), the CPU 51a executes the process of Step S102. When it is determined that the measurement result editing start instruction has been received (YES in Step S107), the CPU 51a executes a test result editing process in Step S108.

Figure 14:
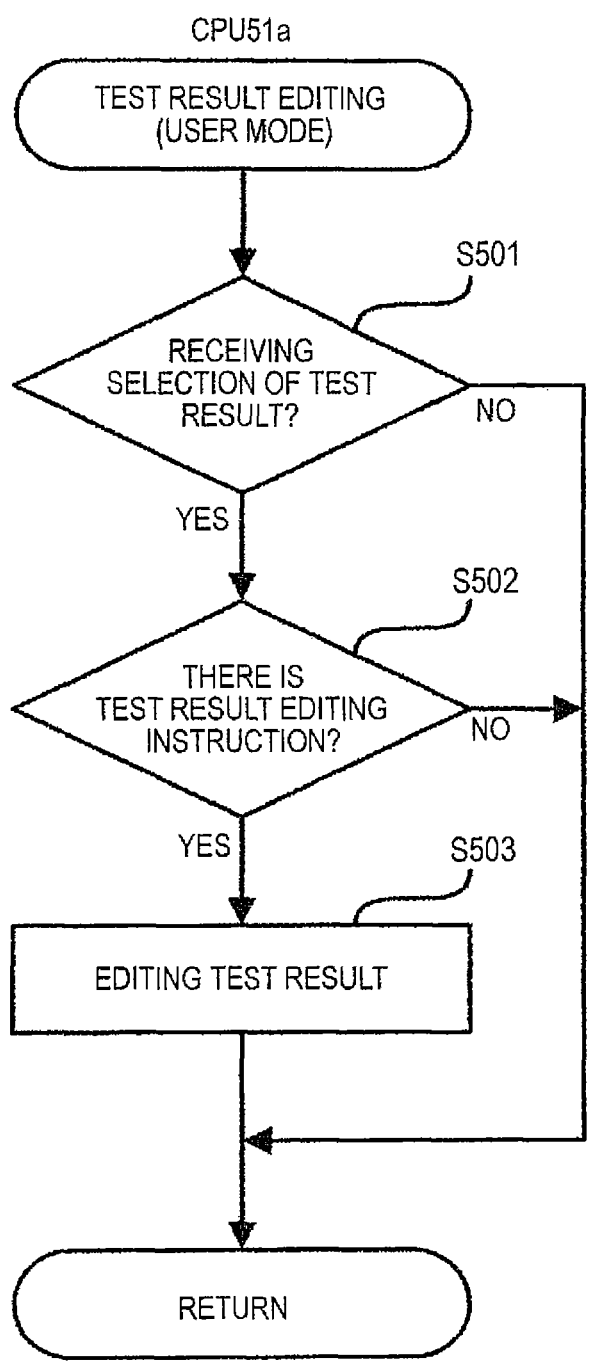
FIG. 14 is a flowchart showing a test result editing process in a user mode according to the first embodiment.

FIG. 14 is a flowchart showing a test result editing process of the control apparatus 5 in a user mode. Hereinafter, the test result editing process of the control apparatus 5 (CPU 51a) in a user mode will be described with reference to FIG. 14. Herein, the editing process is a process of executing the changing and deletion of the contents of test results.

In the outline display field E1 of the test result list screen E which is displayed on the display section 52, test results are displayed as a list in a tabular form. Herein, a row of the table corresponds to one test result registered in the test result database 54c. By selecting a row by the input device 53, an operator can select one corresponding test result. In Step S501, the CPU 51a determines whether the selection of the test result in the outline display field E1 has been received.

By selecting a test result by the input device, the operator can instruct the CPU 51a to edit the selected test result. When it is determined that the selection of the test result has been received (YES in Step S501), the CPU 51a determines in Step S502 whether an instruction for editing the selected test result has been received. By the input device 53, the operator can instruct the CPU 51a of an editing process of the selected test result. The operator can instruct a deletion process of the test result by, for example, pressing a Delete button (not shown) of the input device 53.

When it is determined that the instruction of the editing of the test result has been received (YES in Step S502), in Step S503, the CPU 51a executes on the basis of the received instruction a process of editing the test result for which the editing instruction is issued.

When it is determined that the selection of the test result is not received (NO in Step S501), when it is determined that the instruction of the editing of the test result is not received (NO in Step S502), and when the editing process is executed, the CPU 51a executes the process of Step S102 of the flowchart shown in FIG. 8.

Returning to FIG. 8, when it is determined that the display instruction of the test result list screen E is not received (NO in Step S105), the CPU 51a determines in Step S109 whether an operation history screen G (see FIG. 15) is displayed on the display section 52. When the operation history screen G is not displayed on the display section 52 (NO in Step S109), the CPU 51a determines in Step S110 whether a display instruction of an operation history screen has been received. When it is determined that the display instruction of an operation history screen has been received (YES in Step S110), the CPU 51a displays an operation history screen on the display section 52 in Step S111.

Figure 15:
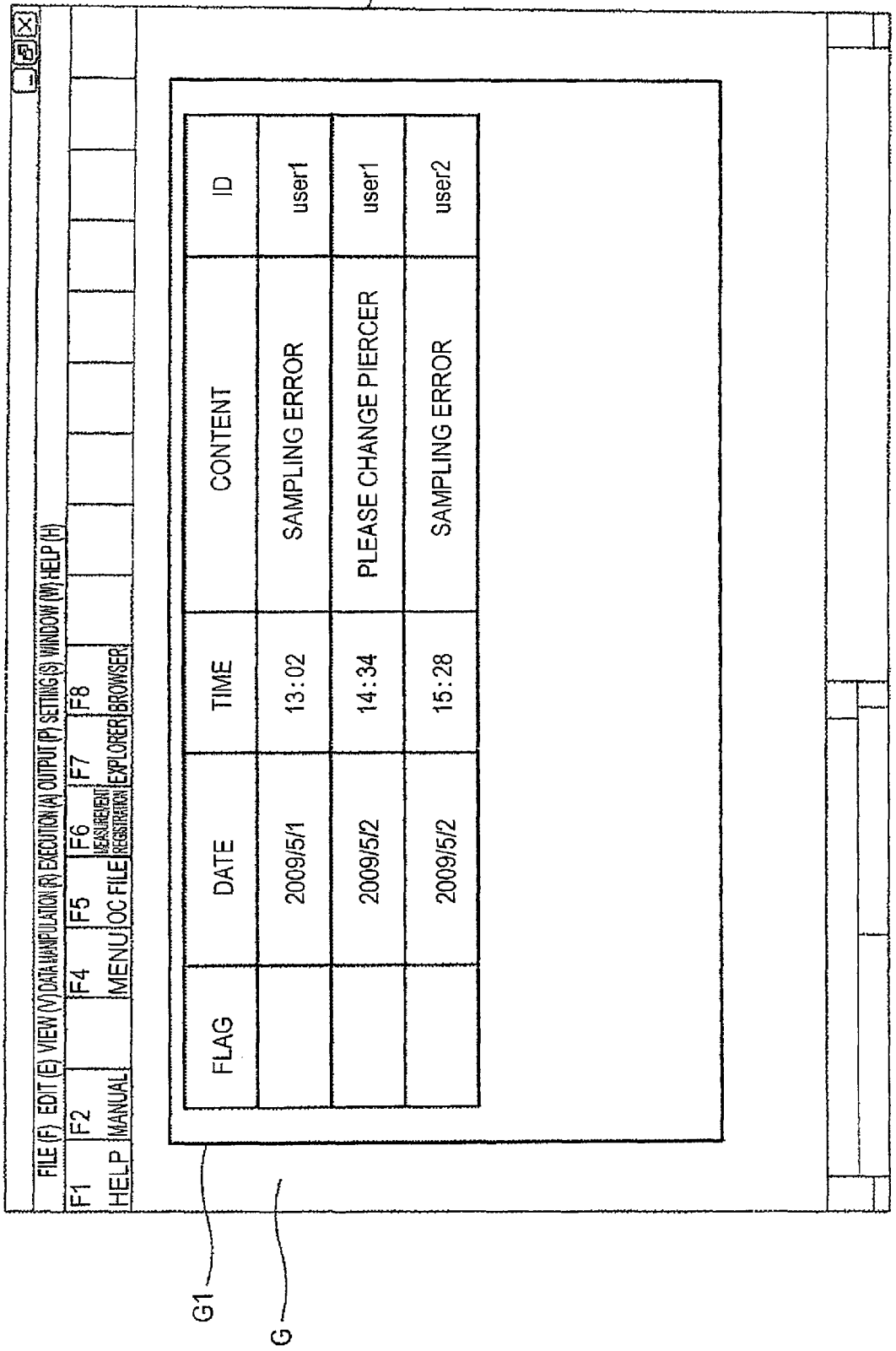
FIG. 15 is a diagram showing an example of an operation history screen which is displayed on the display section in a user mode according to the first embodiment.

FIG. 15 shows the operation history screen G which is displayed on the display section 52 in a user mode. The operation history screen G includes an operation history list field G1 in which an operation history list is displayed, as shown in FIG. 15.

Returning to FIG. 8, when the operation history screen G is displayed on the display section 52 (YES in Step S109) and when the operation history screen G is caused to be displayed on the display section 52, the CPU 51a executes the process of Step S102.

When it is determined that the display instruction of the operation history screen G is not received (NO in Step S110), the CPU 51a determines in Step S112 whether an instruction of logoff has been received. When it is determined that the instruction of logoff has been received (YES in Step S112), the CPU 51a executes a logoff process in Step S113. Then, the CPU 51a executes the process of Step S10 of the flowchart shown in FIG. 5. When it is determined that the instruction of logoff is not received, the CPU 51a executes the process of Step S102.

Figure 16:
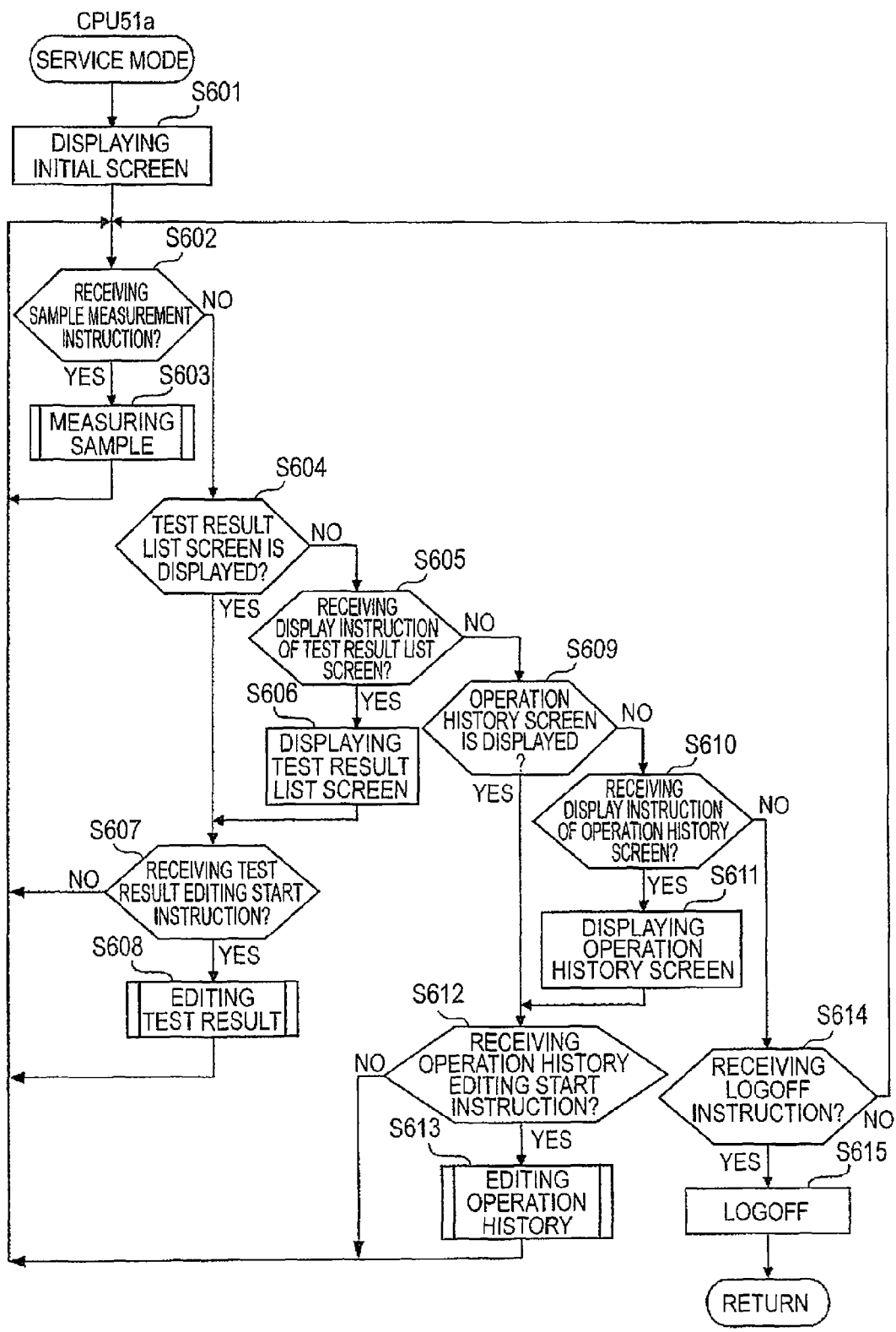
FIG. 16 is a flowchart showing a process of the CPU in a service mode according to the first embodiment.

FIG. 16 is a flowchart showing a process of the CPU 51a in a service mode.

Hereinafter, the process of the control apparatus 5 (CPU 51a) in a service mode will be described with reference to FIG. 16.

In Step S601, the CPU 51a displays an initial screen 521 (see FIG. 17) on the display section 52.

Figure 17:
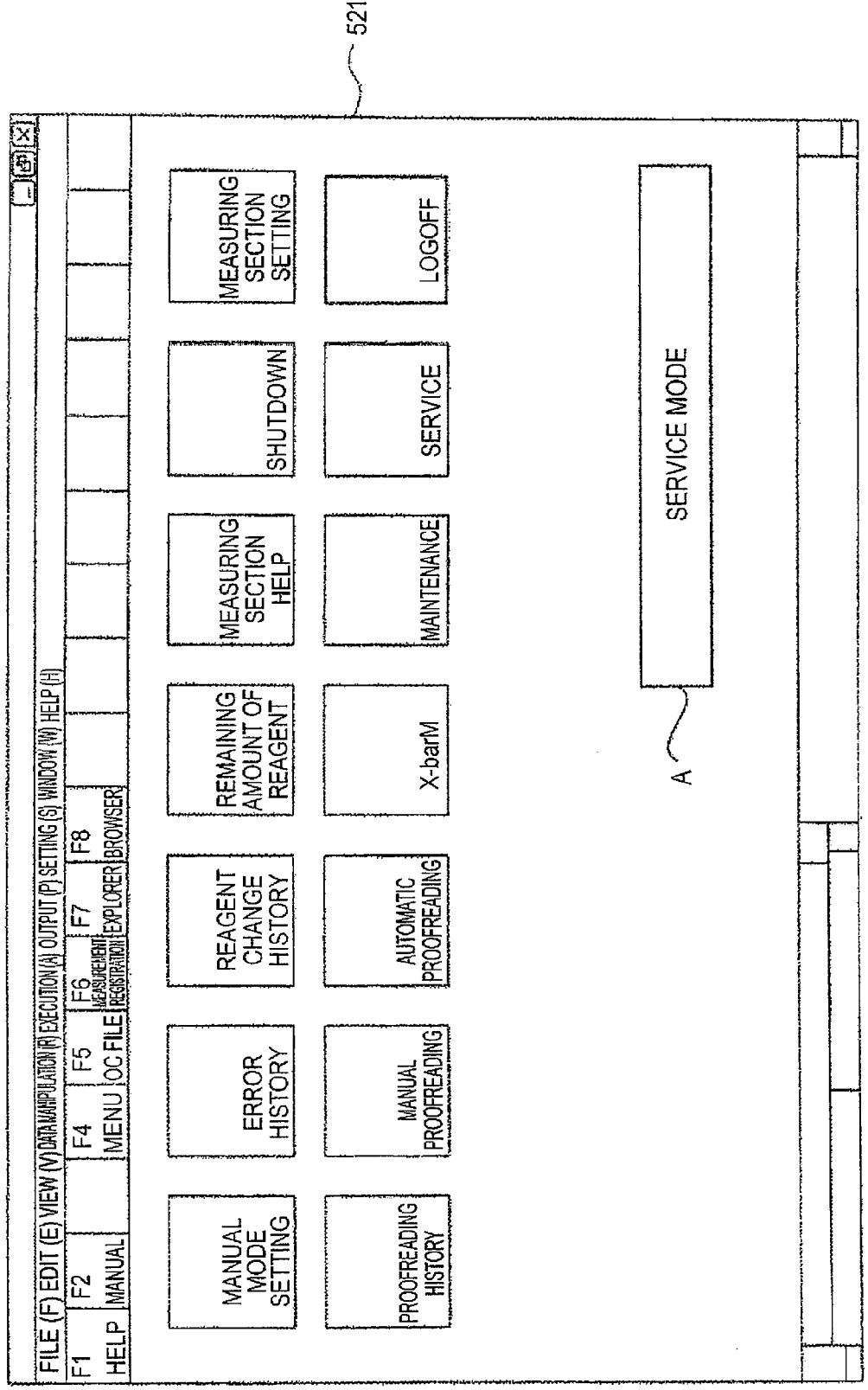
FIG. 17 is a diagram showing an example of an initial screen which is displayed on the display section in a service mode according to the first embodiment.

FIG. 17 is a diagram showing an example of the initial screen 521 which is displayed on the display section 52 in a service mode. Herein, all the display screens in a service mode, that is, the initial screen 521 (see FIG. 17), a test result display screen B (see FIG. 18), a test result list screen E (see FIG. 19), an error screen K (see FIG. 21), an operation history screen G (see FIG. 22) and an error screen L (see FIG. 24) include a mode display bar A showing that a current operator is a serviceman. In addition, the mode display bar A is movable on the display section 52. By the input device 53, an operator can freely move the mode display bar A on the display section 52.

Returning to FIG. 16, in Step S602, the CPU 51a determines whether a sample measurement instruction from an operator has been received. When it is determined that the sample measurement instruction has been received (YES in Step S602), the CPU 51a executes a sample measurement process in Step S603. In the related sample measurement, the serviceman performs a measurement operation on a control specimen and confirms a measurement result of the specimen and an operation history of the apparatus to confirm whether the blood cell analysis apparatus 1 is operating normally.

Figure 18:
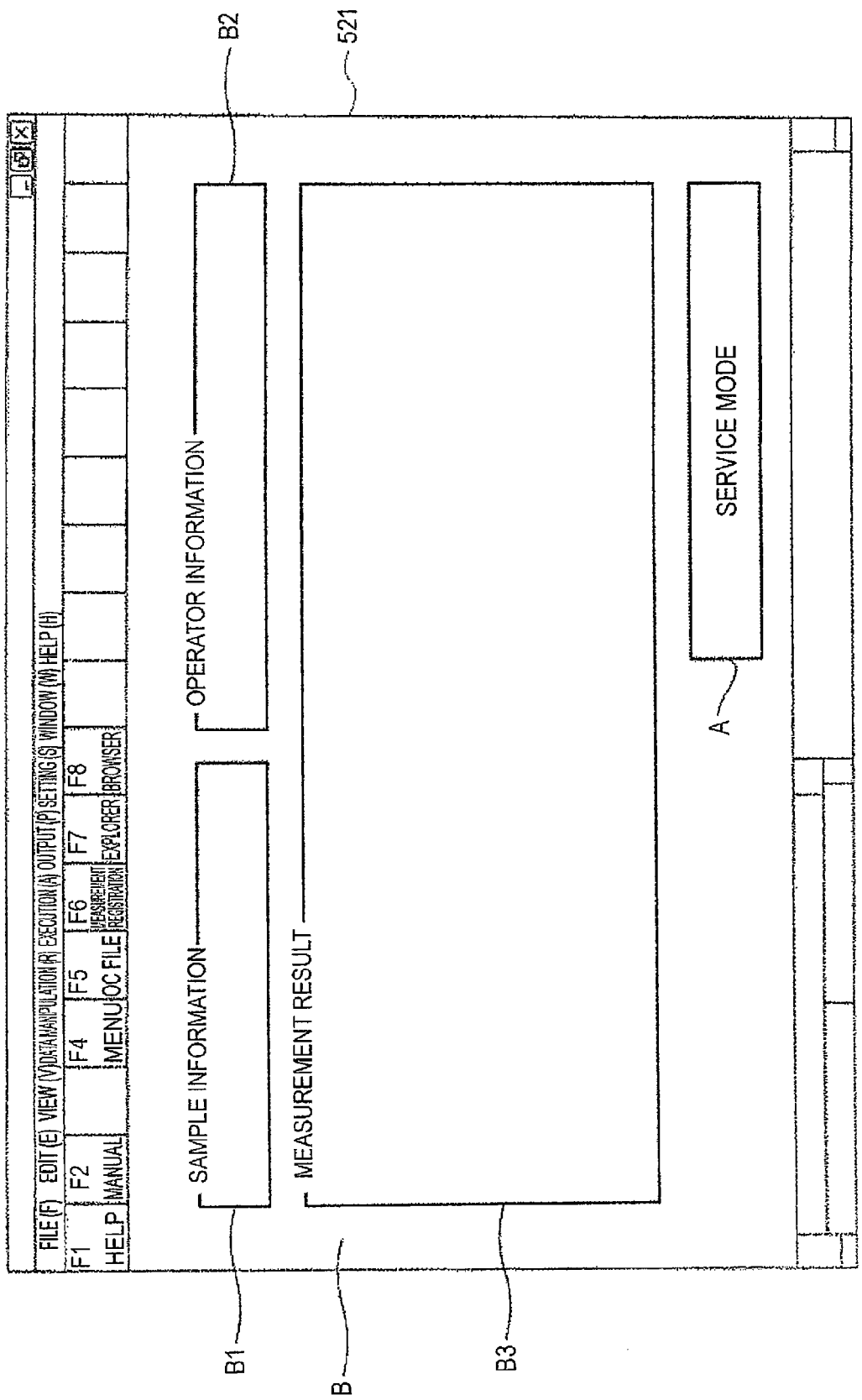
FIG. 18 is a diagram showing an example of a measurement result screen which is displayed on the display section in a service mode according to the first embodiment.

FIG. 18 is a diagram showing an example of the test result display screen B which is displayed on the display section 52 in a service mode. The process of Step S603 is almost the same as the process of Step S103 of the flowchart shown in FIG. 8, except that the CPU 51a displays on the display section 52 the test result display screen B shown in FIG. 18.

Returning to FIG. 16, when it is determined that the sample measurement instruction is not received (NO in Step S602), the CPU 51a determines in Step S604 whether the test result list screen E (see FIG. 19) is displayed on the display section 52. When the test result list screen E is not displayed on the display section 52 (NO in Step S604), the CPU 51a determines in Step S605 whether a display instruction of the test result list screen E has been received.

When it is determined that the instruction for displaying the test result list screen E has been received (YES in Step S605), the CPU 51a displays the test result list screen E on the display section 52 in Step S606.

Figure 19:
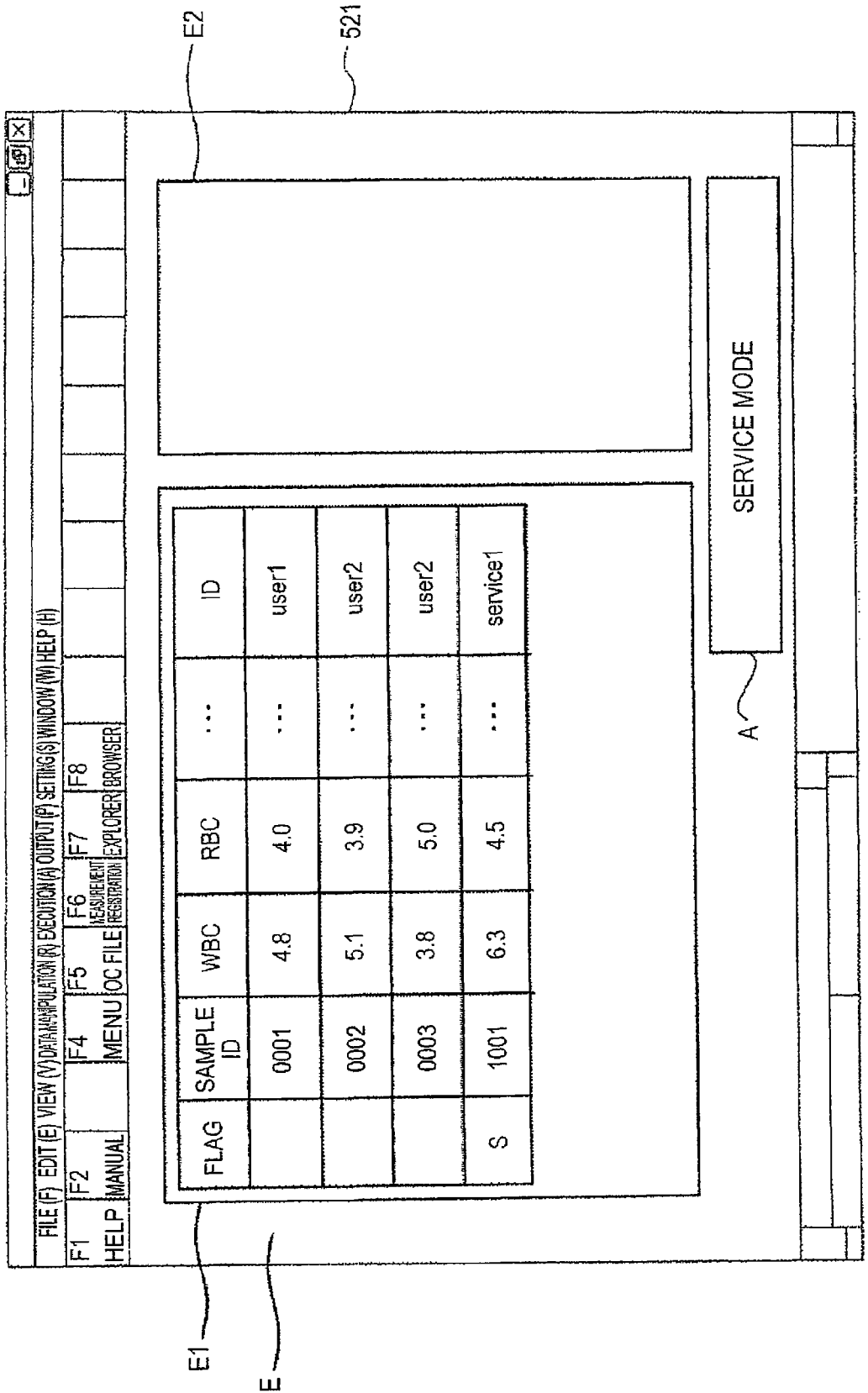
FIG. 19 is a diagram showing an example of a test result list screen which is displayed on the display section in a service mode according to the first embodiment.

FIG. 19 is a diagram showing an example of the test result list screen E which is displayed on the display section 52 in a service mode. Herein, the CPU 51a displays an S mark in a flag column of the test result corresponding to an ID of the serviceman by referring to the operator information database 54b in an outline display field E1 in which outlines of test results are displayed as a list. In this manner, the operator (serviceman) can identify whether each test result is obtained by the serviceman.

Returning to FIG. 16, when the test result list screen E is displayed on the display section 52 (YES in Step S604) and when a process of displaying the test result list screen E on the display section 52 is executed, the CPU 51a determines in Step S607 whether a test result editing start instruction has been received. When it is determined that the test result editing start instruction is not received (NO in Step S607), the CPU 51a executes the process of Step S602. When it is determined that the test result editing start instruction has been received (YES in Step S607), the CPU 51a executes a test result editing process in Step S608.

Figure 20:
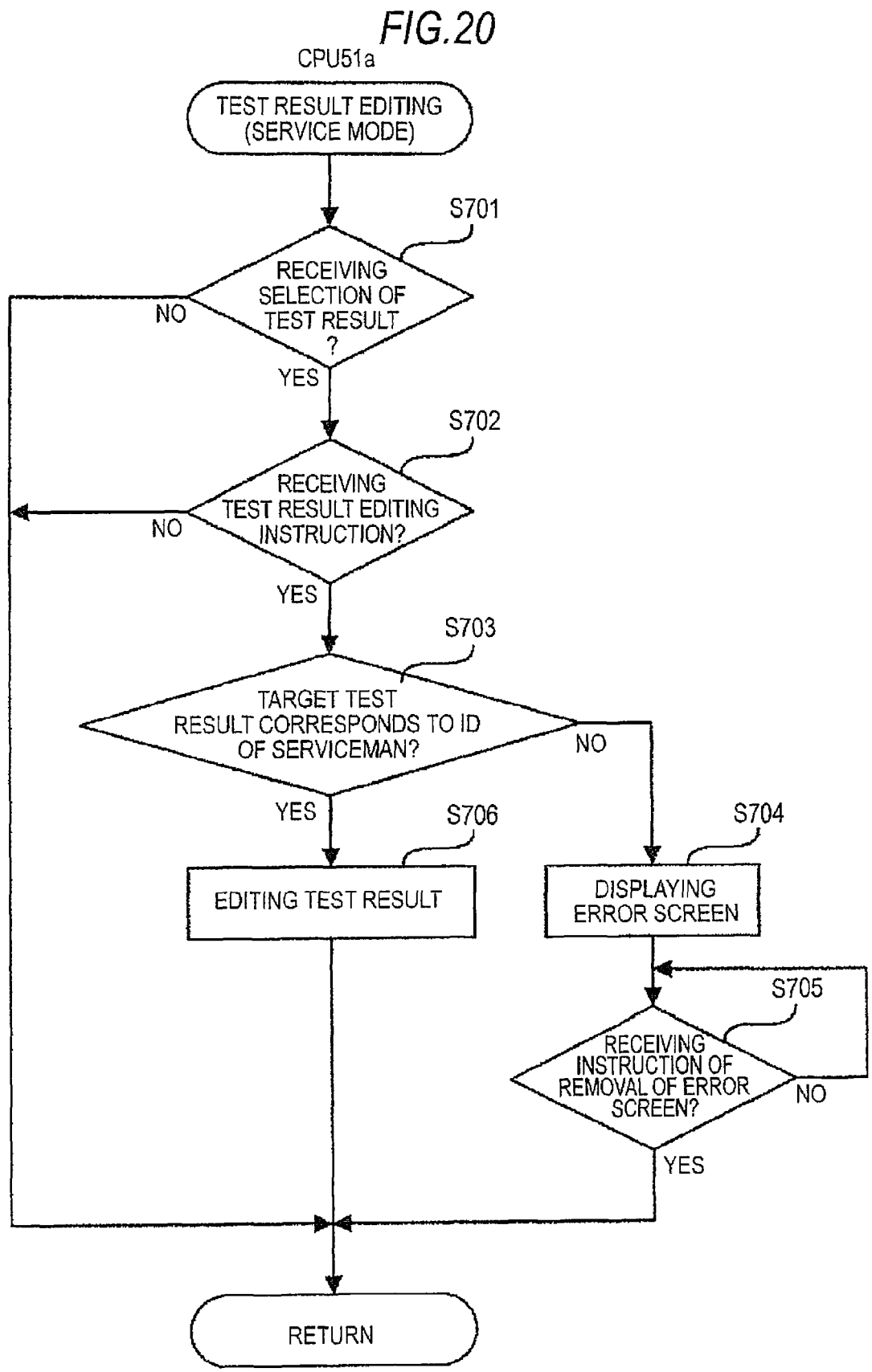
FIG. 20 is a flowchart showing a test result editing process in a service mode according to the first embodiment.

FIG. 20 is a flowchart showing a test result editing process of the control apparatus 5 in a service mode. Hereinafter, the test result editing process of the control apparatus 5 (CPU 51a) in a service mode will be described with reference to FIG. 20. Herein, the editing process is a process of executing the changing and deletion of the contents of test results.

In the outline display field E1 of the test result list screen E which is displayed on the display section 52, test results are displayed as a list in a tabular form. Herein, a row of the table corresponds to one test result registered in the test result database 54c. By selecting a row by the input device 53, an operator can select one corresponding test result. In Step S701, the CPU 51a determines whether the selection of the test result has been received.

By selecting a test result by the input device, the operator can instruct the CPU 51a to edit the selected test result. When it is determined that the selection of the test result has been received (YES in Step S701), the CPU 51a determines in Step S702 whether there is an instruction for editing the selected test result. By the input device 53, the operator can instruct the CPU 51a of an editing process of the selected test result. The operator can instruct the deletion of the test result by, for example, pressing the Delete button (not shown) of the input device 53.

When it is determined that the instruction of the editing of the test result has been received (YES in Step S702), the CPU 51a determines in Step S703 whether the test result for which the editing instruction is issued corresponds to the ID of the serviceman on the basis of whether an S mark is displayed in the flag column. When it is determined that the test result for which the editing instruction is issued does not correspond to the ID of the serviceman (when an S mark is not displayed in the flag column, NO in Step S703), in Step S704, the CPU 51a displays on the display section 52 the error screen K (see FIG. 21) for informing the operator (serviceman) that the target test result cannot be edited.

Figure 21:
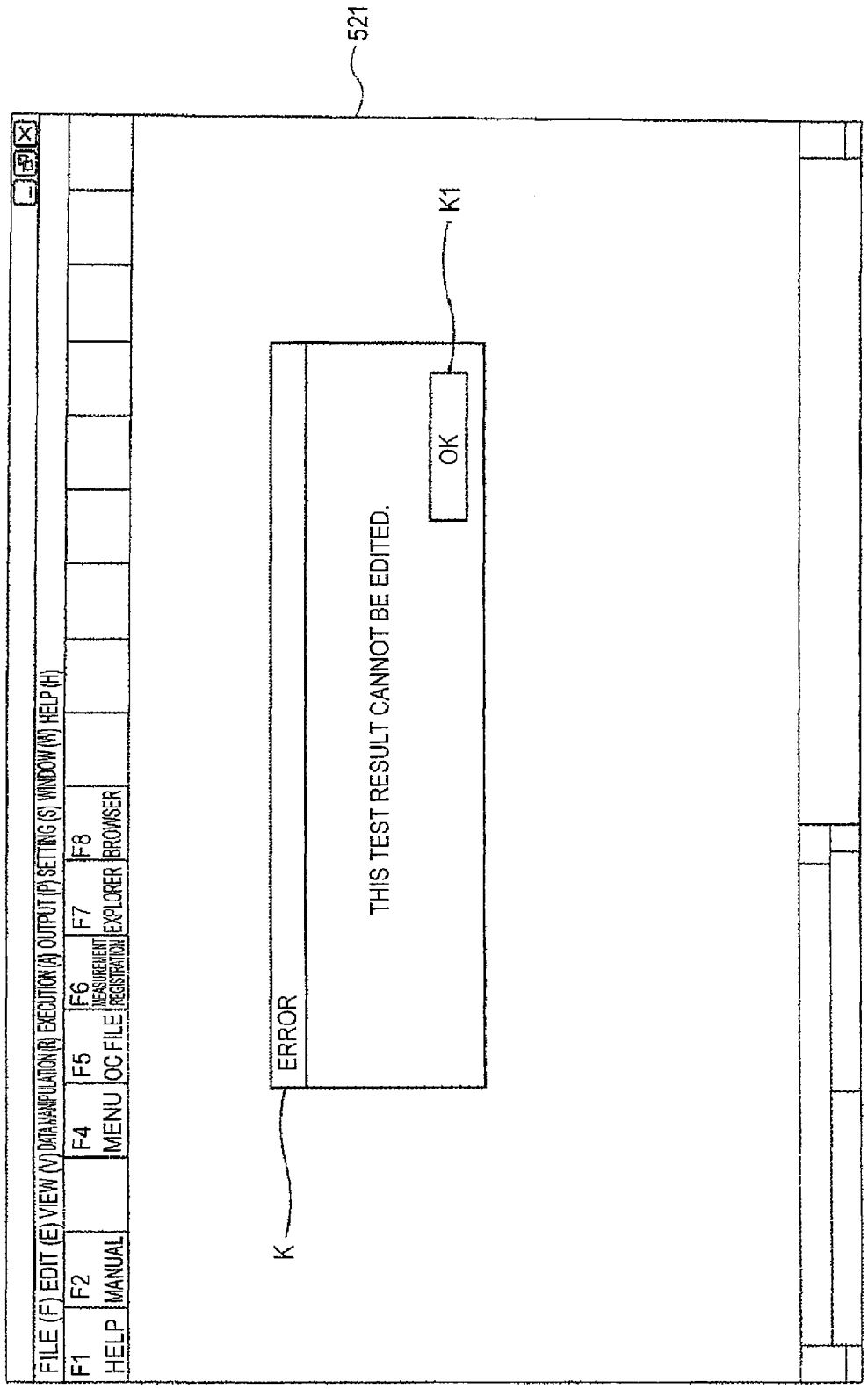
FIG. 21 is a diagram showing an example of an error screen which is displayed on the display section in a service mode according to the first embodiment.

FIG. 21 is a diagram showing an example of an error screen which is displayed on the display section 52. As shown in FIG. 21, the message "this test result cannot be edited" is displayed in the error screen K. The operator selects an OK button K1 by the input device 53 so as to instruct the removal of the error screen.

Returning to FIG. 20, in Step S705, the CPU 51a determines whether the instruction of the removal of the error screen has been received. When it is determined that the instruction of the removal of the error screen has been received (YES in Step S705), the CPU 51a removes the error screen K displayed on the display section 52.

When it is determined that the test result for which the editing instruction is issued corresponds to the ID of the serviceman (when an S mark is displayed in the flag column, YES in Step S703), the editing process is executed on the basis of the instruction in Step S706 and the test result database 54c is updated.

When it is determined that the selection of the test result is not received (NO in Step S701), when it is determined that the instruction of the editing of the test result is not received (NO in Step S702), when it is determined that the instruction of the removal of the error screen has been received, and when the test result database 54c is updated, the CPU 51a executes the process of Step S602 of the flowchart shown in FIG. 16.

Returning to FIG. 16, when it is determined that the display instruction of the test result list screen E is not received (NO in Step S605), the CPU 51a determines in Step S609 whether the operation history screen G (see FIG. 22) is displayed on the display section 52. When the operation history screen G is not displayed on the display section 52 (NO in Step S609), in Step S610, the CPU 51a executes a process of determining whether a display instruction of the operation history screen G has been received. When it is determined that the display instruction of the operation history screen G has been received (YES in Step S610), in Step S611, the CPU 51a executes a process of displaying the operation history screen G on the display section 52.

Figure 22:
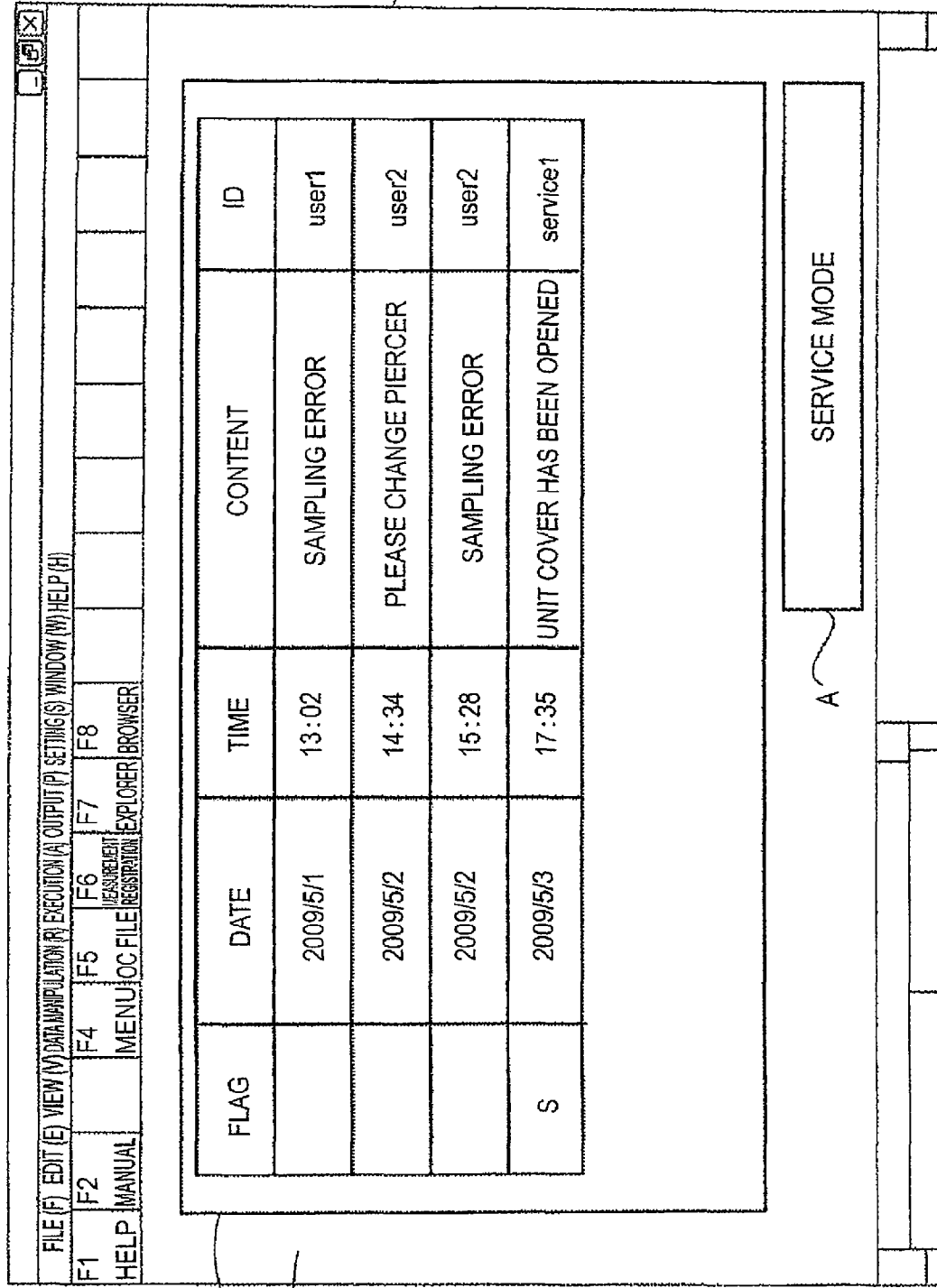
FIG. 22 is a diagram showing an example of an operation history screen which is displayed on the display section in a service mode according to the first embodiment.

FIG. 22 is a diagram showing an example of the operation history screen G which is displayed on the display section 52 in a service mode. Herein, the CPU 51a displays an S mark in a flag column of the operation history corresponding to the ID of the serviceman by referring to the operator information database 54b in an operation history list field G1 in which operation histories are displayed as a list. In this manner, the operator (serviceman) can identify whether each operation history is obtained by the serviceman.

Returning to FIG. 16, when the operation history screen G is displayed on the display section 52 (YES in Step S610) and when a process of displaying the operation history screen G on the display section 52 is executed, the CPU 51a determines in Step S612 whether an operation history editing start instruction has been received. When it is determined that the operation history editing start instruction is not received (NO in Step S612), the CPU 51a executes the process of Step S602. When it is determined that the operation history editing start instruction has been received (YES in Step S612), the CPU 51a executes an operation history editing process in Step S613. Herein, the editing process is a process of executing the changing and deletion of the contents of operation histories.

Figure 23:
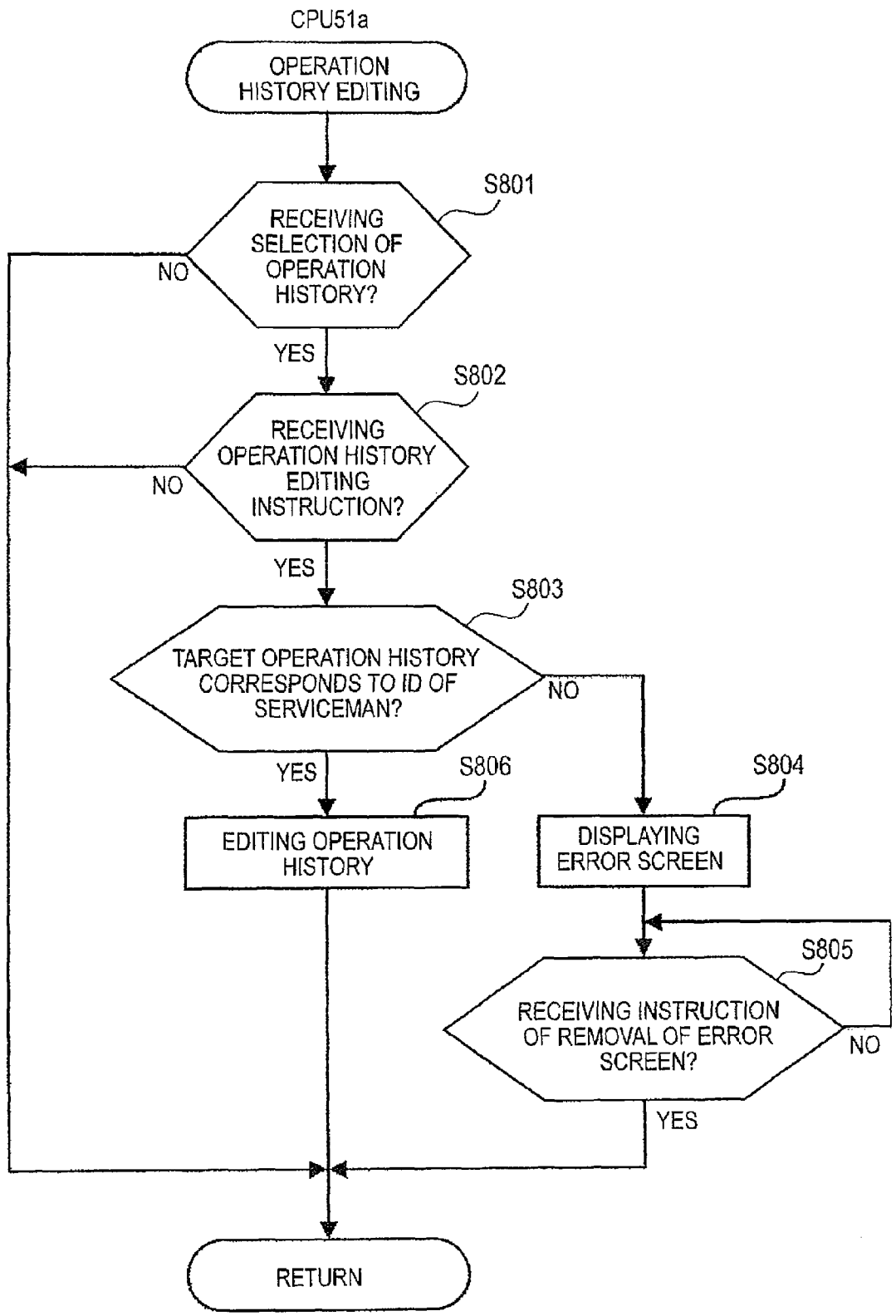
FIG. 23 is a flowchart showing an operation history editing process according to the first embodiment.

FIG. 23 is a flowchart showing an operation history editing process of the control apparatus 5 of the blood cell analysis apparatus 1. Hereinafter, the operation history editing process of the control apparatus 5 (CPU 51a) will be described with reference to FIG. 23.

In the operation history list field G1 of the operation history screen G which is displayed on the display section 52, operation histories are displayed as a list in a tabular form. Herein, a row of the table corresponds to one operation history. By selecting a row by the input device 53, an operator can select one corresponding operation history. In Step S801, the CPU 51a executes a process of determining whether the selection of an operation history has been received.

By selecting an operation history by the input device 53, the operator can instruct the CPU 51a to edit the selected operation history. When it is determined that the selection of the operation history has been received (YES in Step S801), the CPU 51a determines in Step S802 whether an instruction for editing the selected operation history has been received. By the input device 53, the operator can instruct the CPU 51a of an editing process of the selected test results. The operator can instruct the deletion of the operation history by, for example, pressing the Delete button (not shown) of the input device 53.

When it is determined that the instruction of the editing of the operation history has been received (YES in Step S802), the CPU 51a determines in Step S803 whether the operation history for which the editing instruction is issued corresponds to the ID of the serviceman on the basis of whether an S mark is displayed in the flag column. When it is determined that the operation history for which the editing instruction is issued does not correspond to the ID of the serviceman (when an S mark is not displayed in the flag column, NO in Step S803), in Step S804, the CPU 51a displays on the display section 52 the error screen L (see FIG. 24) for informing the operator (serviceman) that the target operation history cannot be edited.

Figure 24:
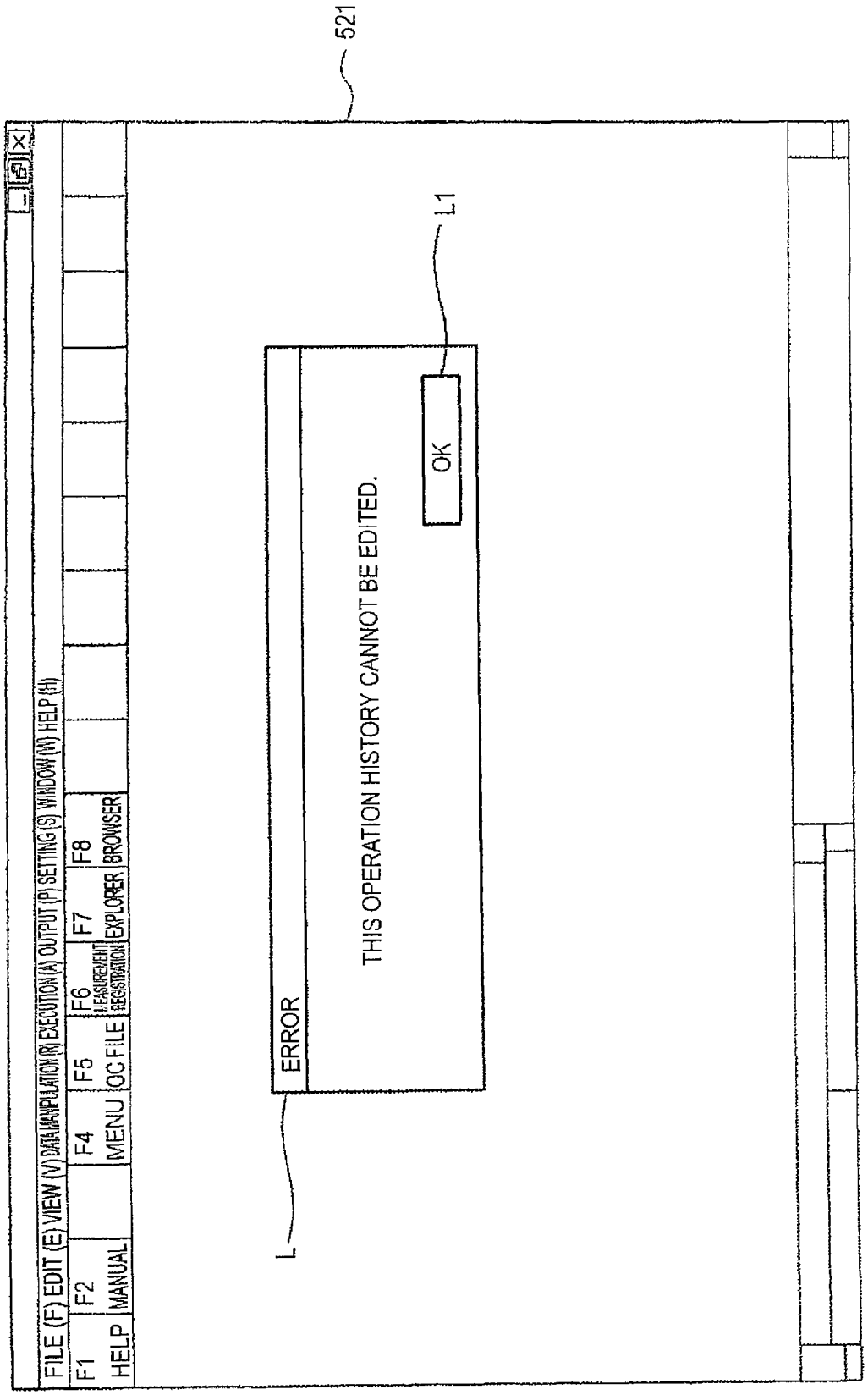
FIG. 24 is a diagram showing an example of an error screen which is displayed on the display section in a service mode according to the first embodiment.

FIG. 24 is a diagram showing an example of the error screen L which is displayed on the display section 52 in a service mode. As shown in FIG. 24, the message "this operation history cannot be edited" is displayed in the error screen L. The operator selects an OK button L1 by the input device 53 so as to instruct the removal of the error screen.

Returning to FIG. 23, in Step S805, the CPU 51a determines whether the instruction of the removal of the error screen has been received. When the instruction of the removal of the error screen has been received (YES in Step S804a), the CPU 51a removes the error screen L displayed on the display section 52.

When it is determined that the operation history for which the editing instruction is issued corresponds to the ID of the serviceman (when an S mark is displayed in the flag column, YES in Step S803), the CPU 51a executes the editing process in Step S806 and updates the operation history database 54d.

When it is determined that the selection of the operation history is not received (NO in Step S801), when it is determined that the instruction of the editing of the operation history is not received (NO in Step S802), when it is determined that the instruction of the removal of the error screen has been received, and when the operation history database 54d is updated, the CPU 51a executes the process of Step S602 of the flowchart shown in FIG. 16.

Returning to FIG. 16, when it is determined that the display instruction of the operation history screen G is not received (NO in Step S610), the CPU 51a determines in Step S614 whether an instruction of logoff has been received. When it is determined that the instruction of logoff has been received (YES in Step S614), the CPU 51a executes a logoff process in Step S615 and then executes the process of Step S10 of the flowchart shown in FIG. 5. When it is determined that the instruction of logoff is not received, the CPU 51a executes the process of Step S602.

As described above, the blood cell analysis apparatus 1 according to this embodiment is configured so that when a serviceman edits a test result and an operation history, it is determined whether the test result and the operation history correspond to an ID of the serviceman, and when it is determined that the test result and the operation history do not correspond to the ID of the serviceman, the test result and the operation history cannot be edited. Accordingly, in the blood cell analysis apparatus 1 according to this embodiment, there is no concern that test results and operation histories which are obtained by a general user will be deleted by mistake when the serviceman deletes a test result and an operation history which are generated with the maintenance work.

Second Embodiment

Hereinafter, a sample testing apparatus according to a second embodiment will be described. The sample testing apparatus according to the second embodiment is the same as the sample testing apparatus according to the first embodiment, except that when a logoff process is executed in a service mode, a test result and an operation history corresponding to an ID of a serviceman can be collectively deleted.

Figure 28:
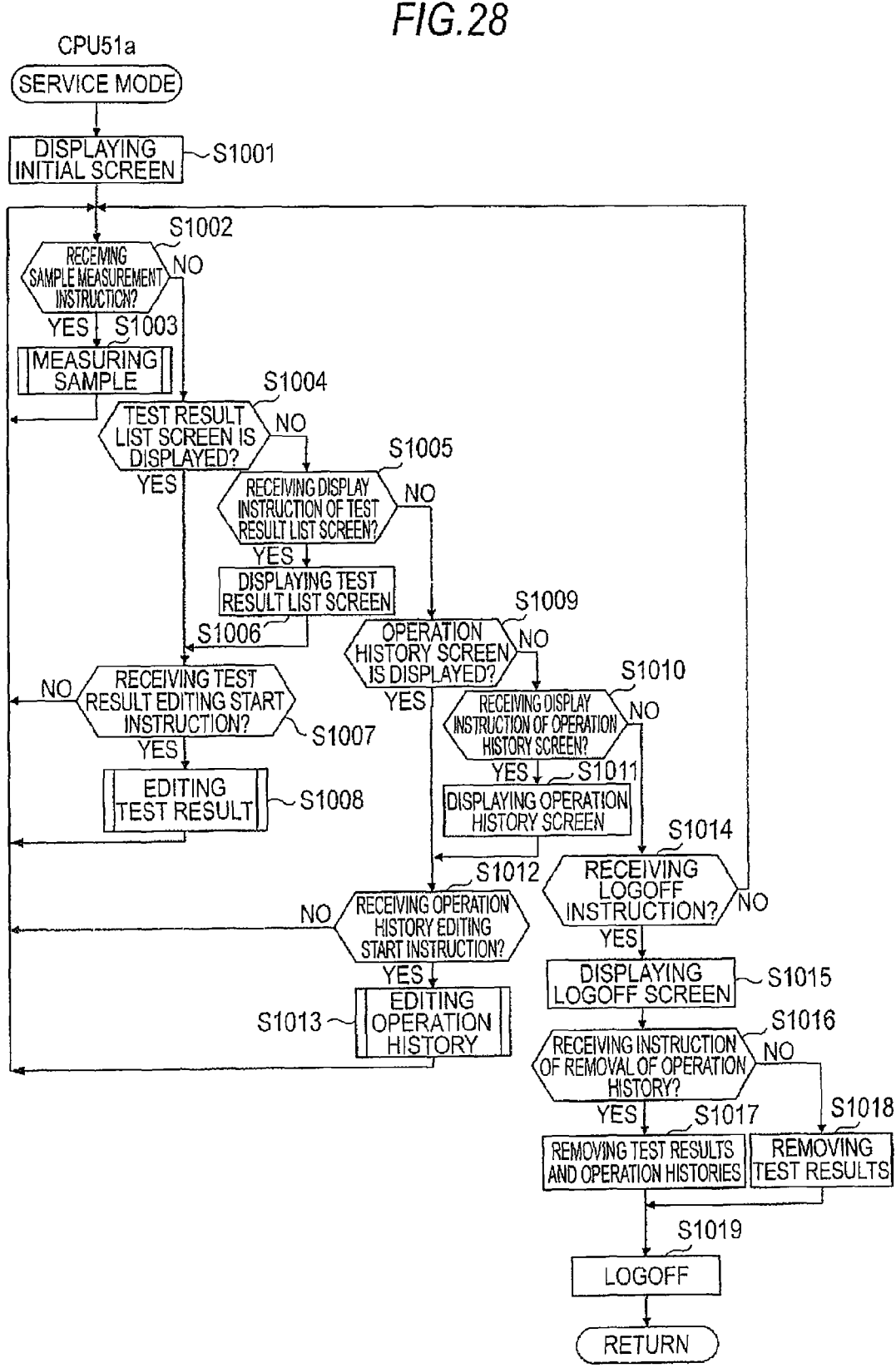
FIG. 28 is a flowchart showing a process in a service mode according to a second embodiment.

FIG. 28 is a flowchart showing a process in a service mode. Hereinafter, the process of the control apparatus 5 (CPU 51a) in a service mode will be described with reference to FIG. 28.

Herein, since Steps S1001 to S1014 and Step S1019 are the same as Steps S601 to S614 and Step S615 of the flowchart shown in FIG. 16, respectively, descriptions thereof will be omitted.

In Step S1015, the CPU 51a displays a logoff screen H (see FIG. 29) on the display section 52.

Figure 29:
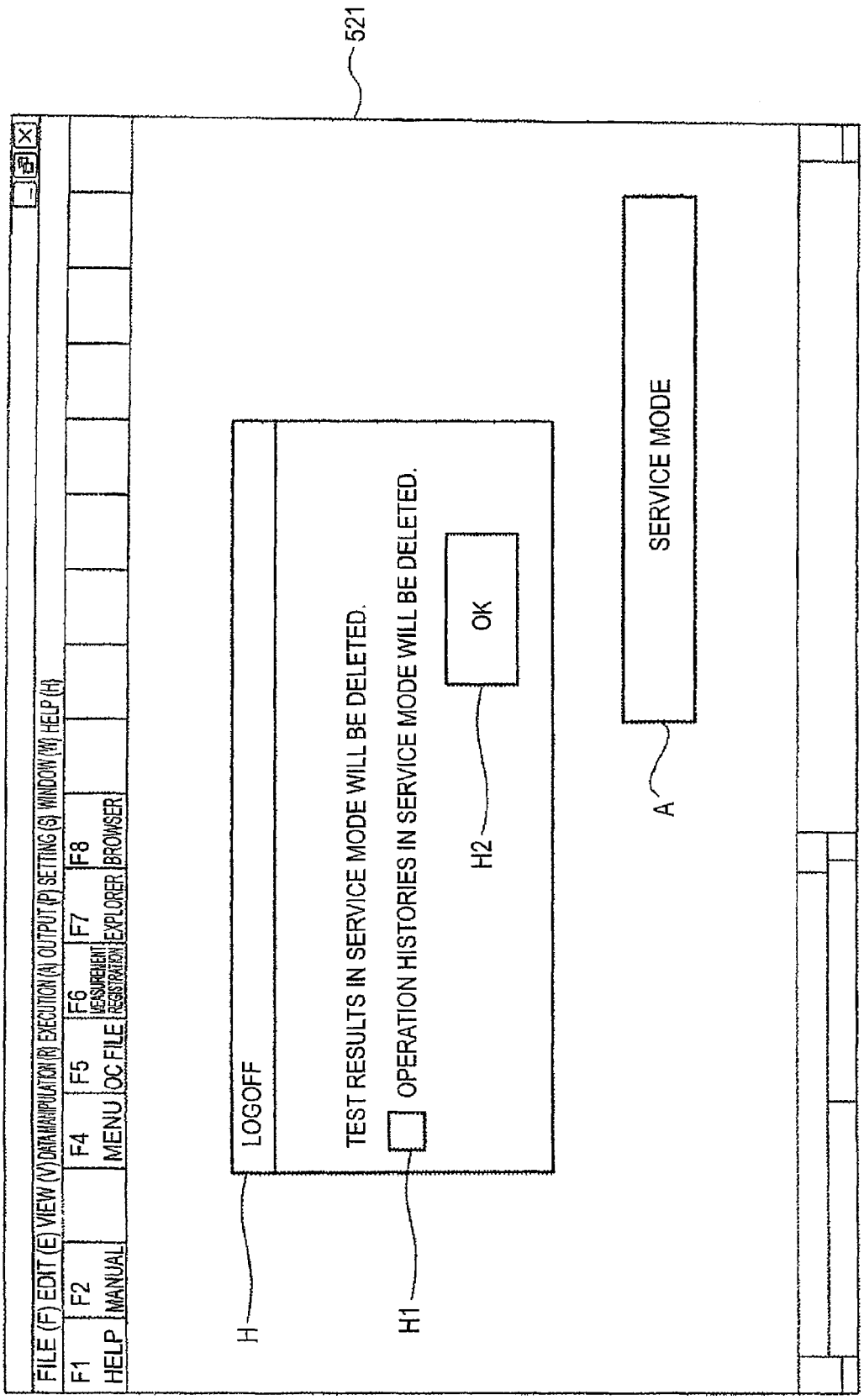
FIG. 29 is a diagram showing an example of a logoff screen which is displayed on the display section in a service mode according to the second embodiment.

FIG. 29 is a diagram showing an example of the logoff screen H which is displayed on the display section 52 in a service mode. As shown in FIG. 29, the message "the test result in the service mode will be deleted" is displayed in the logoff screen H. In addition, the logoff screen H includes a check box H1 and an OK button H2.

Returning to FIG. 28, in Step S1016, the CPU 51a determines whether an operation history deletion instruction has been received. An operator selects the check box H1 by the input device 53 and presses the OK button H2 so as to instruct the CPU 51a of the operation history deletion. Herein, when the operator does not select the check box H1 but selects the OK button H2 by the input device 53, the operation history deletion instruction with respect to the CPU 51a is not carried out. In this manner, in this embodiment, the deletion of the operation history in a service mode is selectable. Accordingly, a general user and a manager as operators on the facility side can confirm on the basis of the operation history which operation was executed in the maintenance work by the serviceman as an operator on the trader side.

When it is determined that the operation history deletion instruction has been received (YES in Step S1016), in Step S1017, the CPU 51a deletes all the test results and operation histories corresponding to the ID of the serviceman from the test result database 54c and the operation history database 54d. In addition, when it is determined that the operation history deletion instruction is not received (NO in Step S1016), in Step S1018, the CPU 51a deletes all the test results corresponding to the ID of the serviceman from the test result database 54c.

As described above, the blood cell analysis apparatus 1 according to this embodiment is configured so that when a logoff process is executed in a service mode operation, a test result corresponding to an ID of a serviceman, or a test result and an operation history corresponding to the ID of the serviceman can be deleted from the test result database 54c and the operation history database 54d. Accordingly, in the sample testing apparatus according to this embodiment, it is possible to save for the serviceman the time to delete the test result and the operation history generated by maintenance work.

The blood cell analysis apparatus 1 according to this embodiment is not limited to the above-described configuration and may have a configuration so that when it is determined that a logoff instruction has been received in Step S1014, the CPU 51a automatically and collectively deletes a test result and an operation history corresponding to the ID of the serviceman from the test result database 54c and the operation history database 54d and then executes a logoff process.

Third Embodiment

Hereinafter, a sample testing system according to a third embodiment will be described. In the sample testing system according to the third embodiment, a plurality of sample testing apparatuses according to the first or second embodiment, which are installed in facilities such as hospitals, and a server computer, which is installed in a support center, are connected to each other via a network. Herein, the support center is a facility in which servicemen are always resident as operators on the trader side delivering apparatuses to facilities such as hospitals.

Figure 30:
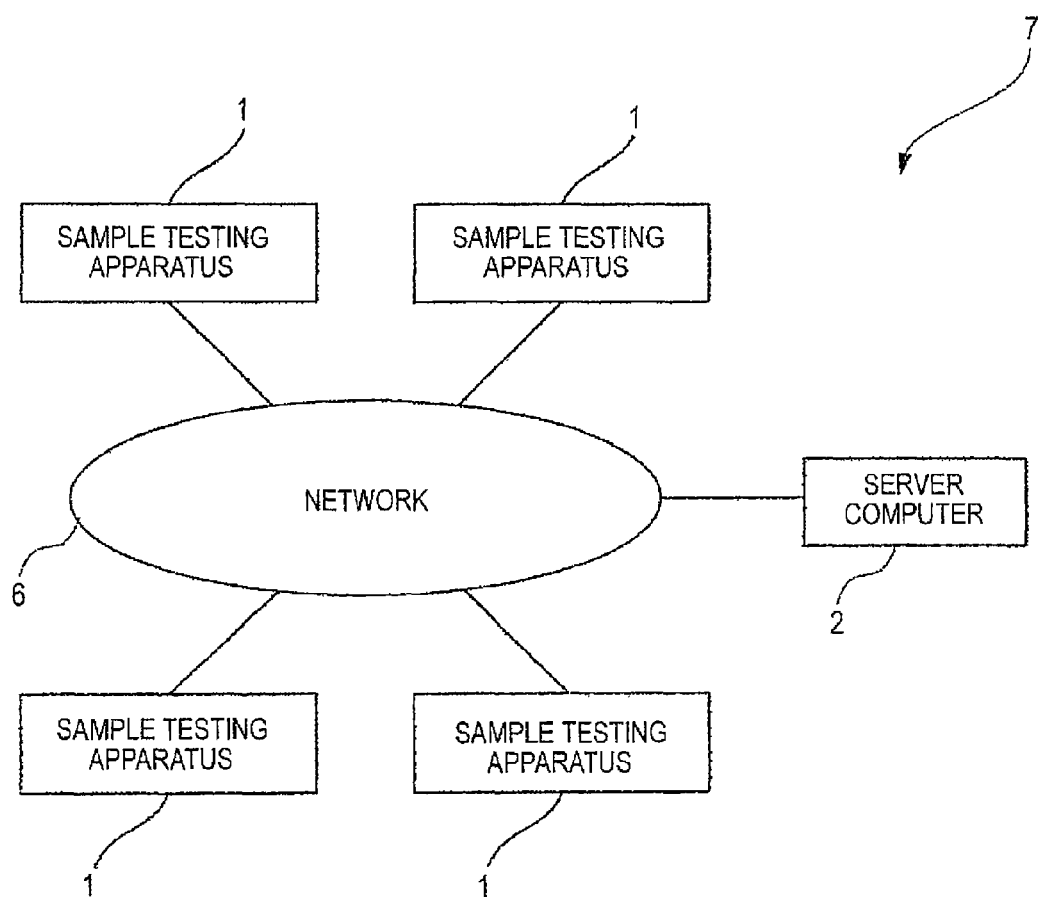
FIG. 30 is a schematic diagram showing the configuration of a sample testing system according to a third embodiment.

FIG. 30 is a schematic diagram showing the configuration of a sample testing system 7 according to the third embodiment. As shown in FIG. 30, in the sample testing system 7, a plurality of blood cell analysis apparatuses 1, which are installed in facilities such as hospitals, are connected to a server computer 2, which is installed in a support center, via a network 6. The server computer 2 manages operation histories in a user mode and test results and operation histories of control specimens in a service mode. In the server computer 2, the test result database shown in FIG. 26 and the operation history database shown in FIG. 27 are provided for each blood cell analysis apparatus 1.

The blood cell analysis apparatus 1 according to the first embodiment transmits operation histories in a user mode and test results and operation histories of control specimens in a service mode to the server computer 2 at predetermined timing. For example, in urgent situations, the apparatus promptly transmits the test results and operation histories, and in less urgent situations, the apparatus transmits the test results and operation histories at the time of logoff or shutdown. In addition, the blood cell analysis apparatus 1 according to the second embodiment transmits test results and operation histories of control specimens in a service mode to the server computer 2 when executing a logoff process in addition to the predetermined timing, and then deletes the transmitted test results and operation histories.

The server computer 2 receives the operation histories in a user mode and the test results and the operation histories of the control specimens in a service mode, which are transmitted from the blood cell analysis apparatus 1, and stores the received test results and operation histories in the test result database and the operation history database corresponding to the blood cell analysis apparatus 1 transmitting them.

As described above, the sample testing system 7 according to this embodiment is configured so that operation histories in a user mode of the blood cell analysis apparatus 1 according to the first and second embodiments and test results and operation histories of control specimens in a service mode are managed by the server computer 2 installed in the support center. Accordingly, in the sample testing system 7 according to this embodiment, states of the blood cell analysis apparatuses 1, each of which is installed in a facility, and situations of maintenance work of the apparatuses can be monitored in the support center.

Other Embodiments

It should be considered that the disclosed embodiments are examples in all aspects but do not restrict the invention. The scope of the invention is defined by the claims and not by the above description.

For example, in the above-described embodiments, the sample testing apparatus is a blood cell analysis apparatus, but the invention is not limited thereto. In the invention, the sample testing apparatus may be a blood coagulation measurement apparatus, a blood image analysis apparatus, an in-urine physical component analysis apparatus, a biochemical analysis apparatus or an immunoassay apparatus.

In addition, in the above-described embodiments, a sample container 100 held in a rack 101 is transported to the sample setting section 355a by the transport apparatus 4, but the invention is not limited thereto. In the invention, the sample container 100 may be directly disposed in the sample setting section 355a by an operator.

In the above-described embodiments, test results and operation histories are stored in association with identification information (ID) of an operator in the test result database 54c and the operation history database 54d, but the invention is not limited thereto. For example, test results and operation histories may be stored in association with at least one of identification information (ID) of an operator and information indicating a group to which the operator belongs in the test result database 54c and the operation history database 54d.

In the above-described embodiments, a process in a user mode is executed when a group corresponding to a received ID is a general user group or a manager group, but the invention is not limited thereto. For example, when the group corresponding to the received ID is a manager group, a process in a manager mode may be executed. In the manager mode, for example, a process of setting a function which can be executed for each general user may be executed by a manager.

What is claimed is:

1. A biological sample testing apparatus, the apparatus comprising:

a controller that operates the testing apparatus in one of a user mode and a service mode, the controller including a first memory and a second memory, the first memory storing first identification information of a first operator in association with first attribute information and second identification information of a second operator in association with second attribute information, wherein the first attribute information indicates a general operator and the second attribute information indicates a person in charge of maintenance work;

an identification information receiving device that receives an input of at least one of the first and second identification information of one of the first and second operators;

a testing means for obtaining user mode test results and service mode test results by testing a sample under the direction of the controller in either the service mode or the user mode, wherein the second memory stores each of a plurality of user mode and service mode test results obtained by the testing means so as to be linked with at least one of the first identification information and the second identification information received by the identification information receiving device;

an operation end instruction receiving means for receiving a logoff instruction for ending a use of the sample testing apparatus by at least one of the first and the second operators; and a deleting means for automatically selecting a service mode test result linked with the second identification information from the plurality of service mode and user mode test results, deleting the selected service mode test result and preventing from deleting the user mode test result linked with the first identification information in response to receiving the logoff instruction, so as to avoid inadvertent deletion of the user mode test result in a case where the identification information receiving device has received the second identification information.

2. The sample testing apparatus of claim 1, wherein in the case where the identification information receiving device has received the second identification information, the deleting means automatically deletes all of the service mode test results linked with the second identification information in response to receiving the logoff instruction.

3. The sample testing apparatus of claim 1, wherein the second memory stores an operation history of the testing section so as to be linked with at least one of the first identification information and the second identification information received by the identification information receiving device, and wherein in the case where the identification information receiving device has received the second identification information, the deleting means automatically deletes the operation history linked with the second identification information in response to receiving the logoff instruction.

4. The sample testing apparatus of claim 3, further comprising:

a deletion instruction receiving means for receiving a deletion instruction of the service mode test results and the operation history when the logoff instruction has been received by the operation end instruction receiving means;

wherein the deleting means deletes the service mode test results and the operation history linked with the second identification information in response to receiving the deletion instruction by the deletion instruction receiving means.

5. The sample testing apparatus of claim 3, wherein in the case where the identification information receiving device has received the second identification information, the deleting means automatically deletes all of operation history which are stored so as to be linked with the second identification information.

6. The sample testing apparatus of claim 1, wherein the first memory further stores third identification information of a third operator in association with third attribute information.

7. The sample testing apparatus of claim 6, wherein the third attribute information indicates a manager of the apparatus.

8. A biological sample testing apparatus, the apparatus comprising:
a controller that operates the testing apparatus in one of a user mode and a service mode, the controller including a first memory and a second memory,
the first memory storing first identification information of a first operator in association with first attribute information and second identification information of a second operator in association with second attribute information,
wherein the first attribute information indicates a general operator and the second attribute information indicates a person in charge of maintenance work;
an identification information receiving device that receives an input of at least one of the first and second identification information of one of the first and second operators;
a testing means that obtains user mode test results and service mode test results by testing a sample under the direction of the controller in either the user mode or the service mode,
wherein the second memory stores each of a plurality of user mode and service mode test results obtained by the testing means so as to be linked with at least one of the first identification information and the second identification information received by the identification information receiving device; and
a displaying means for showing the plurality of user mode and service mode test results on a display,
wherein the controller prevents changing or deleting a user test result linked with the first identification information and allows changing or deleting a service mode test result linked with the second identification information, so as to avoid inadvertent deletion of the user test result when the identification information receiving device has received the second identification information.

9. The sample testing apparatus of claim 8, further comprising: a selection receiving device for receiving from the operator a selection of a service mode test result shown by the display, wherein the controller executes a process of changing or deleting the user mode test result selected via the selection receiving device when the selected test result is linked with the second identification information.

10. The sample testing apparatus of claim 9, wherein the controller deletes the service mode test result selected via the selection receiving device.

11. The sample testing apparatus of claim 9, wherein the display means shows a notice on the display for giving notice that the operator belongs to the second attribute when the identification information receiving device has received the second identification information.

12. The sample testing apparatus of claim 9, wherein the display means shows the plurality of service mode test results such that a test result linked with the second identification information can be identified when the identification information receiving device has received the second identification information.

13. A biological sample testing apparatus, the apparatus comprising:
a controller that operates the testing apparatus in one of a user mode and a service mode, the controller including a memory,
the memory storing first identification information of a first operator in association with first attribute information and second identification information of a second operator in association with second attribute information,
wherein the first attribute information indicates a general operator and the second attribute information indicates a person in charge of maintenance work;
a testing section for obtaining a test result by testing a sample under the direction of the controller in either the user mode or the service mode; and
the controller configured to:
receive an input of at least one of the first and second identification information of one of the first and second operators; and
store, in the memory, each of a plurality of user mode and service mode test results obtained by the testing section, so as to be linked with at least one of the received first and second identification information, and
in response to receiving a logoff instruction for ending a use of the sample testing apparatus by the operator and in a case where the controller has received the second identification information, the controller is further configured to automatically select the service mode test results linked with the second identification information from the plurality of test results, delete the selected service mode test results from the memory and prevent deleting the user mode test results linked with the first identification information, so as to avoid inadvertent deletion of the user mode test result.

14. A biological sample testing apparatus, the apparatus comprising:
a controller that operates the testing apparatus in one of a user mode and a service mode, the controller including a memory,
the memory storing first identification information of a first operator in association with first attribute information and second identification information of a second operator in association with second attribute information,
wherein the first attribute information indicates a general operator and the second attribute information indicates a person in charge of maintenance work;
a display;
a testing section for obtaining user mode test results and service mode test results by testing a sample under the direction of the controller in either the user mode or the service mode; and
the controller configured to:
receive an input of at least one of the first and second identification information of one of the first and second operators; and
store, in the memory, each of a plurality of user mode and service mode test results obtained by the testing section, so as to be linked with at least one of the received first and second identification information, and
the controller is further configured to:

show the plurality of user mode and service mode test results on the display; and prevent editing user mode test results linked with the first identification information so as to avoid inadvertent deletion of user test results and allow a process of editing service mode test results linked with the second identification information when the controller has received the second identification information.

15. The sample testing apparatus of claim 14, wherein the controller is further configured to:

receive a selection of a service mode test result shown by the display; and edit the selected service mode test result when the test result is linked with the second identification.

* * * * *